US00RE40233E

(19) United States
(12) Reissued Patent
Locarnini et al.

(10) Patent Number: US RE40,233 E
(45) Date of Reissued Patent: Apr. 8, 2008

(54) VIRAL VARIANTS AND METHODS FOR DETECTING SAME

(75) Inventors: Stephen A Locarnini, East St. Kilda (AU); Angeline I Bartholomeusz, Carnegie (AU); Thein T. Aye, Victoria (AU); Robert A. de Man, Rotterdam (NL)

(73) Assignee: Melbourne Health, Parkville (AU)

(21) Appl. No.: 10/920,462

(22) Filed: Aug. 18, 2004

Related U.S. Patent Documents

Reissue of:
(64) Patent No.: 6,555,311
Issued: Apr. 29, 2003
Appl. No.: 09/306,420
Filed: May 6, 1999

U.S. Applications:
(63) Continuation of application No. PCT/AU97/00520, filed on Aug. 15, 1997.

(30) Foreign Application Priority Data

Nov. 8, 1996 (AU) ..... PO 3519

(51) Int. Cl.
*C12Q 1/70* (2006.01)
*C12N 7/00* (2006.01)

(52) U.S. Cl. ..... 435/5; 435/235.1
(58) Field of Classification Search ..... 435/5, 435/235.1, 193, 194; 424/189.1, 227.1
See application file for complete search history.

(56) References Cited

U.S. PATENT DOCUMENTS

| | | | |
|---|---|---|---|
| 2003/0124096 | A1 | 7/2003 | Locamini |
| 2006/0165725 | A1 | 7/2006 | Bozdayi |
| 2006/0234212 | A1 | 10/2006 | Bozdayi |
| 2007/0042356 | A1 | 2/2007 | Schildgen |

FOREIGN PATENT DOCUMENTS

| | | |
|---|---|---|
| WO | 94/26904 | 11/1994 |
| WO | WO 94/26904 | 11/1994 |
| WO | 97/40193 | 10/1997 |
| WO | WO 98/21317 | 5/1998 |
| WO | WO 00/58477 | 10/2000 |
| WO | WO 00/61758 | 10/2000 |
| WO | 03/066841 | 8/2003 |
| WO | 03/087351 | 10/2003 |
| WO | 2004/0321224 | 4/2004 |

OTHER PUBLICATIONS

Aye et al (Hepatology vol. 24 No. 4 pt. 2, abstract 633, 1996).*
Fischer et al (Antimicrobial Agents & Chemotherapy 40:1957–1960, Aug. 1996).*
Weiss et al (Virology 216:214–218, Feb. 1, 1996).*
Poch et al (EMBO Journal 8:3867–3874, 1989).*
Tipples et al (Hepatology 24(3): 714–717, Sep. 1996).*
Ling et al (Hepatology 24(3): 711–713, Sep. 1996).*
Nature(1979), vol. 282, Pasek M et al, pp. 575–579, "Hepatitis B virus genes and their expression in *E. Coli*" Figure 2.
Nucleic Acids Research(1983), vol. 11(6), Ono Y et al, pp. 1747–1757, "The complete nucleotide of the cloned hepatitis B virus DNA; subtype *adr* and *adw*" Figure 2 and 3.
J. General Virology (1988), vol. 69, Vaudin M et al, pp. 1383–1389, "The complete nucleotide sequence of the genome of a hepatitis B virus isolated from a naturally infected chimpanzee" Figure 1.
J. General Virology (1988), vol. 69, Okamoto F et al, pp. 2575–2583, "Typing hepatitis B virus by homology in nucleotide sequence: comparison of surface antigen subtypes" Figure 1.
Gene (1988), vol. 64, Rivkina M et al, pp. 285–296, "Nucleotide sequence of integrated hepatitis B virus DNA and human flanking regions in the genome of the PLC/PRF/5 cell line" Figure 5.
J General Virology (1992), vol. 73(5), Norder H et al, pp. 1201–1208, "Comparison of the amino acid sequences of nine different scrotypes of hepatitis B surface antigen and genomic classification of the corresponding hepatitis B strains" Figure 3.
J General Virology (1993), vol. 74, Norder H et al, pp. 1341–1348, "Genetic relatedness of hepatitis B viral strains of diverse geographical origin and natural variations in the primary structure of the surface antigen" Figure 2.
J Medical Virology (1994), vol. 44(1), Horikita M et al, pp. 96–103, "Differences in the entire nucleotide sequence between hepatitis B virus genomes from carriers positive for antibody to hepatitis B e antigen with and without active disease" Table IV.
Research in Virology (1995), vol. 146(6), Ni F et al, pp. 397–407, "A new immune escape mutant of hepatitis B virus with an Asp to Ala substitution in aa144 of the envelope major protein" Figure 3.
GenBank Accession No. D50489, "Hepatitis B virus DNA, complete genome".
J General Virology (1995), vol. 45, Uchida T et al, pp. 247–252, Complete nucleotide sequences and the characteristics of two hepatitis B virus mutants causing serologically negative acute or chronic hepatitis B: p. 249.
J General Virology (1996), vol. 3, Alexopoulou A et al, pp. 173–181, "Whole genome analysis of hepatitis B virus from four cases of fulminant hepatitis: genetic variability and its potential role in disease pathogenicity" Table 3.

(Continued)

*Primary Examiner*—Mary E. Mosher
(74) *Attorney, Agent, or Firm*—Nixon & Vanderhye P.C.

(57) ABSTRACT

The present invention relates generally to viral variants exhibiting reduced sensitivity to particular agents and/or reduced interactivity with immunological reagents. More particularly, the present invention is directed to hepatitis B variants exhibiting complete or partial resistance to nucleoside analogues and/or reduced interactivity with antibodies to viral surface components. The present invention further contemplates assays for detecting such viral variants which assays are useful in monitoring anti-viral therapeutic regimes.

41 Claims, 10 Drawing Sheets

OTHER PUBLICATIONS

Figure 1:
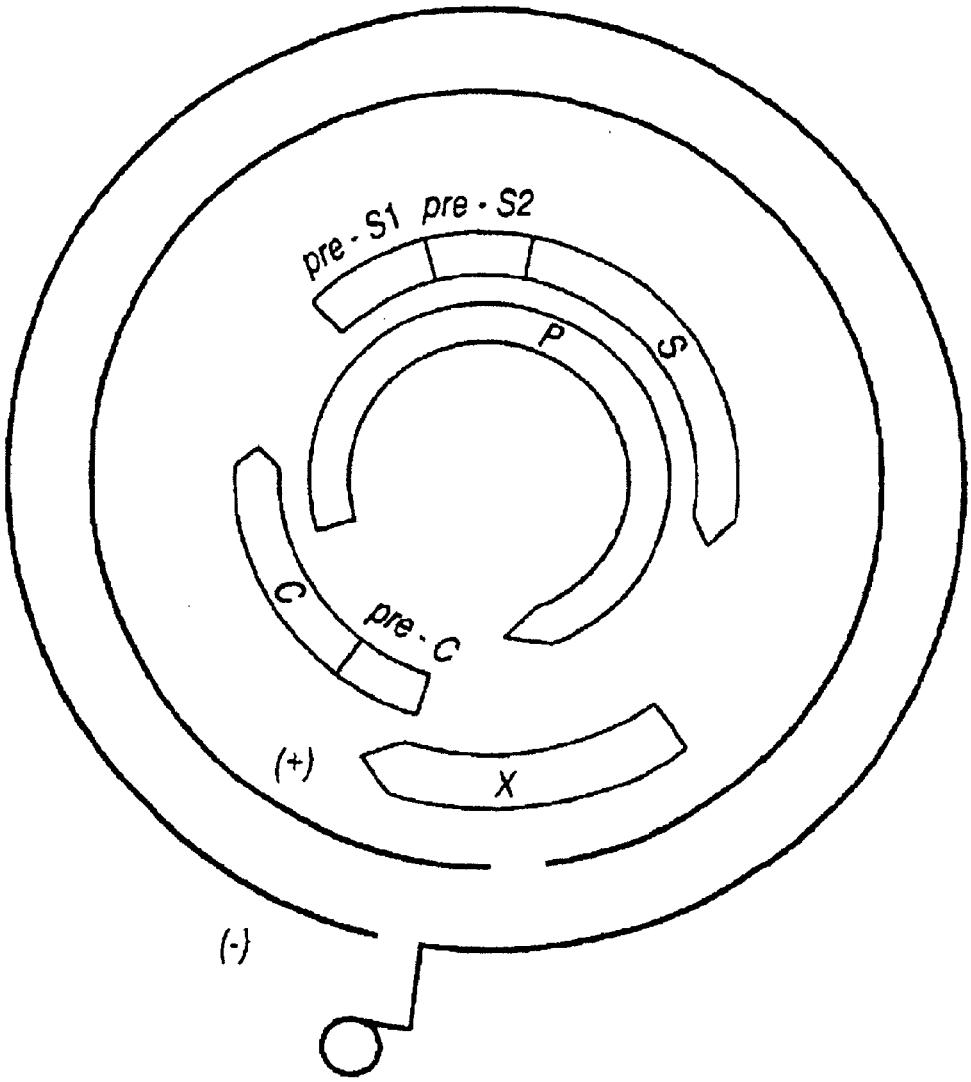

J General Virology (1997), vol. 78, Bowyer S et al, pp. 1719–1729, "A unique segment of the hepatitis B virus group A genotype identified in isolates from South Africa" Figure 5.
Ling et al, "Selection of mutations in the hepatitis B virus . . . ", Hepatology Sep. 1996 24(3):711–3.
Tipples et al, "Mutation in HBV RNA—Dependent DNA . . . ", Hepatology vol. 24, No. 3, 1996, pp. 714–717.
Carman et al, "Vaccine–induced escape mutant . . . ", The Lancet, vol. 336, 1990 (8711) pp. 325–329.
Fujii et al, "Gly$^{145}$ to Arg Substitution in HBs Antigen of . . . ", Biochemical and Biophysical Research Communications, vol. 184, No. 3, May 15, 1992, pp. 1152–1157.
Yamamoto et al, "Naturally Ocurring Escape Mutants of Hepatitis B Virus with . . . ", Journal of Virology, vol. 68, No. 4, Apr. 1994, pp. 2671–2676.
Carman, "The clinical significance of surface antigen variants . . . ", Journal of Viral Hepatitis, 1997. 4 (Suppl. 1) 11–20.
Wang GT et al, Chung Hua I Hseuh Tsa Chih Jun. 1994 74(6) pp. 355–357, 391 (PubMed English Abstract PMID 7994645).
Ren H et al, Chung Hua I Hseuh Tsa Chih 1995 75(7) pp. 396–398 (PubMed English Abstract PMID 7553156).
Chenault (Biochimie 76:3–8, 1994).
Fischer (Antimicrobial Agents and Chemotherapy 40(8): 1957–1960, Aug. 1996.
Norder (Virology 198: 489–503, 1994).
Bartholomew (Lancet 349: 20–22, Jan. 1997).
Aye et al, Hepatology vol. 24, No. 4, Pt.2, Sep. 1996.
Delaney et al, Antiviral Chemistry & Chemotherapy 12:1–35 (2001).
Aye et al, Journal of Hepatology, 1997; 26: 1148–1153.
de Man et al, Journal of Hepatology, 1998; 29: 669–675.
Norder et al, Journal of General Virology 1992, vol. 73, pp. 3141–3145.
Ho et al, Clinical and Diagnostic Laboratory Immunology, 1995, vol. 2, No. 6, pp. 760–762.
Bartholomeusz et al, 1997, International Antiviral News, vol. 5, No. 8, pp. 123–124.
Aoyama & Partners letter dated Oct. 10, 2007 containing translation of Office Action dated Sep. 25, 2007 with respect to Japanese Patent Application No. 521944/1998 and correction of translation of Reference No. 6 "Escape Mutants of HBs" (3 pages).
Bozdayi et al "A new mutation pattern (YMDD–<YSDD) in the YMDD motif of HBV–DNA polymerase gene in chronic B hepatitis infection resistant to lamivudine" Journal of Hepatology, 2001, 34(1):162–162, Meeting Abstract.
Delaney et al, "Phenylpropenamide Derivatives AT–61 and AT–130 Inhibit Replication of Wild–Type and Lamivudine–Resistant Strains of Hepatitis B Virus In Vitro", Antimicrobial Agents and Chemotherapy, Sep. 2002, vol. 46, No. 9, pp. 3057–3060.
Gaillard et al, "Kinetic Analysis of Wild–Type and YMDD Mutant Hepatitis B Virus Polymerases and Effects of Deoxyribonucleotide Concentrations on Polymerase Activity", Antimicrobial Agents and Chemotherapy, Apr. 2002, vol. 46, No. 4, pp. 1005–1013.
Gerner et al., "Hepatitis B Virus Core Promoter Mutations in Children with Multiple Anti–HBe/HBeAg Reactivations Result in Enhanced Promoter Activity", Journal of Medical Virology 59:415–423 (1999).
Han et al, "YMDD Motif Mutants in Hepatitis B Virus Polymerase during Lamivudine Therapy", Korean J. Genetics 24(2):219–226 (Jun. 2002).
Niesters et al, "Identification of a new variant in the YMDD motif of the hepatitis B virus polymerase gene selected during lamivudine therapy", J. Med. Microbial., vol. 51 (2002), 695–699.
Perrillo et al, "Adefovir Dipivoxil Added to Ongoing Lamivudine in Chronic Hepatitis B With YMDD Mutant Hepatitis B Virus", Gastroenterology 2004; 126:81–90.
Stoll–Becker et al, "Transcription of Hepatitis B Virus in Peripheral Blood Mononuclear Cells from Persistently Infected Patients", Journal of Virology, Jul. 1997, vol. 71, No. 7, pp. 5399–5407.
Stuyver et al, "Nomenclature for Antiviral–Resistant Human Hepatitis B Virus Mutations in the Polymerase Region", Hepatology 2001; 33:751–757.
Tatti et al, "Mutations in the conserved woodchuck hepatitis virus polymerase FLLA and YMDD regions conferring resistance to lamivudine", Antiviral Research 55 (2002) 141–150.
Torresi et al, "Restoration of Replication Phenotype of Lamivudine–Resistant Hepatitis B Virus Mutants by Compensatory Changes in the "Fingers" Subdomain of the Viral Polymerase Selected as a Consequence of Mutations in the Overlapping S Gene", Virology 299, 88–99 (2002).
Wakefield et al, "In Vitro Enzymatic Activity of Human Immunodeficiency Virus Type 1 Reverse Transcriptase Mutants in the Highly Conserved YMDD Amino Acid Motif Correlates with the Infectious Potential of the Proviral Genome", Journal of Virology, Nov. 1992, vol. 66, No. 11, pp. 6806–6812.
Werle et al "Evolution of hepatitis B virus load and viral genome sequence during adefovir dipivoxil therapy" 2004, Journal of Viral Hepatitis, vol. 11, No. 1, pp. 74–83.
Yan, L. et al, Accession No. Q9IF40, submitted (JUN–2000), title: "Direct Submission", http://www.ncbi.nlm.nih.gov.
Blum, "Variants of Hepatitis B, C and D Viruses: Molecular Biology and Clinical Significance", Digestion (1995); 56:85–95.
Kidd–Ljunggren, "Variability in Hepatitis B Virus DNA: Phylogenetic, Epidemiological and Clinical Implications", Scand J Infect Dig 28:111–116 (1996).
Kan Tan Sui, "Escape Mutants of HBs" (1993), 27(4), pp. 555–562.
H. Uetake Ed., Virology, 4$^{th}$ Ed., ver. 1, Rikougaku–sha (publ.), Jul. 10, 2002, p. 452 (in Japanese) (Relevance noted in Doc. No. 61).
Aoyama & Partners letter dated Feb. 15, 2007, relating to Japanese Patent Application No. 521944/1998 (4 pages).
Aoyama & Partners letter dated Jan. 25, 2007, relating to Japanese Patent Application No. 521944/1998 (2 pages).
Aoyama & Partners letter dated Jul. 23, 2007, relating to Japanese Patent Application No. 521944/1998 (1 page) with English translation of amended claims (2 pages) and copy of Amendment filed Jul. 19, 2007, in response to Official Action (11 pages).

* cited by examiner

```
                        DOMAIN A
                        (421)          (437)
HBV(Pre-treatment)      SDLSWLSLDVSAAFYH
HBV(Post-treatment)     SDLSWLSLDVSAAFYH
WHV                     TDLQWLSLDVSAAFYH
HIV                     KKKSVTVLDVGDAYFS

                                        DOMAIN B
                          (498)   (505)         (519)  (526) (529)
HBV(Pre-treatment)      QTFGRKLHLYSHPIILGFRKIPMGVGLSPFLLAQFTSAICS
HBV(Post-treatment)     QTFGRKLHLYSHPIILGFRKIPMGLGLSLFLMAQFTSAICS
WHV                     KTYGRKLHLLAHPFIMGFRKLFMGVGLSPFLLAQFTSALAS
HIV                     --------------RYQYNVLPQGWKGSPAIFQSSMTKILE

HSV                     TTIGREMLL-ATREYVHAR-----WAAFEQLLADF--PEAA

                          DOMAIN C
                        (546)     (556)
HBV(Pre-treatment)      AFSYMDDVVLG
HBV(Post-treatment)     AFSYMDDVVLG
WHV                     VFAYMDDLVLG
HIV                     IYQYMDDLYVG
```

Fig.3

DOMAIN A 421 430 440 450

$S^{N}_{D}$LSWLSLD VSAAFYH$^{I}_{P}$PL HPAAMPHLL$^{I}_{V}$ GSSGL$^{S}_{D}$RYVA 460 470 480 490

RLSS$^{T}_{N}$S$^{R}_{N}$N$_{I}$*N $^{N}_{Y}$H$^{Q}$Y$^{H}$R$^{G}$***$^{D}_{N}$LH $^{D}_{N}$S$_{Y}$CSR$^{N}_{Q}$LYVS L$^{L}_{M}$LLY$^{K}_{Q}$T$^{Y}_{F}$G$^{R}_{W}$

DOMAIN B 500 510 520 530

KLHL$^{Y}$L$^{S}_{A}$HPI$^{I}_{V}$ LGFRK$^{I}_{L}$PMG$^{V}_{G}$ GLSPFLLAQF TSAI$^{C}_{L}$A$^{A}_{S}$V$^{V}_{M}$V$^{V}_{T}$R$^{R}_{C}$R

DOMAIN C 540 550 560

AF$^{F}_{P}$HC$^{L}_{V}$A$^{A}_{V}$F$^{S}_{A}$Y MDD$^{V}$L$_{M}$VLGA$^{K}_{R}$S$^{S}_{T}$ V$^{V}_{G}$Q$^{Q}_{E}$H$^{L}$S$_{R}$E$^{S}_{F}$L$^{L}_{Y}$F$^{F}_{A}$T$^{T}_{S}$A

DOMAIN D DOMAIN E 570 580 590 600

V$^{V}_{I}$T$^{T}_{C}$N$^{N}_{S}$F$^{F}_{V}$LL$^{S}_{D}$L$^{L}_{V}$GI HLNP$^{N}_{Q}$KTKRW GYSLNFMGY$^{V}_{I}$I G

*Fig.4*

DOMAIN B (509) (512) (519) (526) (533)

HBV(consensus) $^{S}_{A}$HPI$^{I}_{V}$LGFRK$^{I}_{L}$PMG$^{V}_{G}$GLSPFLLAQFTSAICS HBV(patient A) QTFGRKLHLYSHPIIL GFRKIPMGLGLSLFLMAQFTSAICS
HBV(patient B) QTFGRKLHLYSHPIIL GFRKIPMGVGLSPFLMAQFTSAICS
HBV(3TC 1) QTFGRKLHLYSHPIIL GLRKIPMGVGLSPFLMAQFTSAICS
HBV(patient C-FCV) QTFGRKLHLYSHPIVL GFRKIPMGVGLSPFLLAQFTSALCS

DOMAIN C 550 (559)

HBV(CONSENSUS) $^{A}_{V}$F$^{S}_{A}$YMDD$^{V}_{LM}$VLGA$^{K}_{R}$$^{S}_{T}$
HBV(patient A) AFSYMDD V VLG
HBV(patient B) AFSYMDD V VLG
HBV(3TC 1) AFSY$^{V}_{I}$DD V VLG
HBV(patient C-FCV) AFSYMDD V VLG
HBV(patient C 3TC) AFSYMDD V VLGAKT

Fig.5

```
            *     *     *     *     *     *
        TCTTCCAATT TGTCCTGGTT ATCGCTGGAT
pol      S  S  N   L  S  W  L   S  L  D
HBsAG     L  P  I   C  P  G   Y  R  W  M

            *     *     *     *     *     *
        CATCCTGCTG CTATGCCTCA TCTTCTTATT
         H  P  A   A  M  P  H   L  L  I
          I  L  L   L  C  L  I   F  L  L

            *     *     *     *     *     *
        CGTTTGTCCT CTAATTCCAG GATCAACAAC
         R  L  S   S  N  S  R   I  N  N
          V  C  P   L  I  P   G  S  T  T

            *     *     *     *     *     *
        AGGCAACTCT ACGTTTCCCT CATGTTGCTG
         R  Q  L   Y  V  S  L   M  L  L
          G  N  S   T  F  P   S  C  C  C

            *     *     *     *     *     *
        TATTCCCATC CCATCGTCCT GGGCTTTCGC
         Y  S  H   P  I  V  L   G  F  R
          I  P  I   P  S  S   W  A  F  A
```

Fig.6 (i)

```
    *     *     *     *     *     *
GTGTCTGCGG CGTTTTATCA TATTCCTCTT
 V  S  A   A  F  Y  H   I  P  L>
  C  L  R   R  F  I   I  F  L  F>

    *     *     *     *     *     *
GGTTCTTCTG GATTATCAAG GTATGTTGCC
 G  S  S   G  L  S  R   Y  V  A>
  V  L  L   D  Y  Q   G  M  L  P>

    *     *     *     *     *     *
AACATGCAAA ACCTGCACGA CTCCTGCTCA
 N  M  Q   N  L  H  D   S  C  S>
  T  C  K   T  C  T   T  P  A  Q>

    *     *     *     *     *     *
TACAAAACCT ACGGAGAGAA ATTGCACCTG
 Y  K  T   Y  G  E  K   L  H  L>
  T  K  P   T  E  R   N  C  T  C>

    *     *     *     *     *     *
AAAATACCTA TGGGAGTGGG CCTCAGTCCG
 K  I  P   M  G  V  G   L  S  P>
  K  Y  L   W  E  W   A  S  V  R>
```

Fig.6 (ii)

```
     *     *     *     *     *     *
TTTCTCTTGG CTCAGTTTAC TAGTGCCATT
 F  L  L   A  Q  F  T   S  A  I
  F  S  W   L  S  L  L   V  P  F

     *     *     *     *     *     *
TGTTTGGCTT TCAGCTATAT GGATGATGTG
 C  L  A   F  S  Y  M   D  D  V
  V  W  L   S  A  I   W  M  M  W

     *     *     *     *     *     *
GAGGCCCTTT ATACCGCTGT TACCAATTTT
 E  A  L   Y  T  A  V   T  N  F
  R  P  F   I  P  L   L  P  I  F

     *     *     *     *     *     *
AACAAAACAA AAAGATGGGG TTATTCCCTA
 N  K  T   K  R  W  G   Y  S  L
  T  K  Q   K  D  G   V  I  P  *

     *     *
GGAACATTGC
 G  T  L  X>
  E  H  C>
```

Fig.6 (iii)

```
     *     *     *     *     *     *
TGTTCAGTGG TTCGTAGGGC TTTCCCCCAC
 C  S  V   V  R  R  A   F  P  H>
  V  Q  W   F  V  G   L  S  P  T>

     *     *     *     *     *     *
GTATTGGGGG CCAAGTCTGT ACAGCATCGT
 V  L  G   A  K  S  V   Q  H  R>
  Y  W  G   P  S  L  Y   S  I  V>

     *     *     *     *     *     *
CTTTTGTCTC TGGGTATACA TTTAAACCCT
 L  L  S   L  G  I  H   L  N  P>
  F  C  L   W  V  Y   I  *  T  L>

     *     *     *     *     *     *
AACTTCATGG GTTACATAAT TGGAAGTTGG
 N  F  M   G  Y  I  I   G  S  W>
  T  S  W   V  T  *  L   E  V  G>
```

Fig.6 (iv)

VIRAL VARIANTS AND METHODS FOR DETECTING SAME

Matter enclosed in heavy brackets [ ] appears in the original patent but forms no part of this reissue specification; matter printed in italics indicates the additions made by reissue.

This is a continuation of PCT application No. PCT/AU97/00520, filed Aug. 15, 1997.

The present invention relates generally to viral variants exhibiting reduced sensitivity to particular agents and/or reduced interactivity with immunological reagents. More particularly, the present invention is directed to hepatitis B variants exhibiting complete or partial resistance to nucleoside analogues and/or reduced interactivity with antibodies to viral surface components. The present invention further contemplates assays for detecting such viral variants which assays are useful in monitoring anti-viral therapeutic regimes.

Bibliographic details of the publications numerically referred to in this specification are collected at the end of the description. Sequence Identity Numbers (SEQ ID NOs.) for the nucleotide and amino acid sequences referred to in the specification are defined following the bibliography.

Throughout this specification, unless the context requires otherwise, the word "comprise", or variations such as "comprises" or "comprising" or the term "includes" or variations thereof, will be understood to imply the inclusion of a stated element or integer or group of elements or integers but not the exclusion of any other element or integer or group of elements or integers. In this regard, in construing the claim scope, an embodiment where one or more features is added to any of claim is to be regarded as within the scope of the invention given that the essential features of the invention as claimed are included in such an embodiment.

Specific mutations in an amino acid sequence are represented herein as "$Xaa_1nXaa_2$" where $Xaa_1$ is the original amino acid residue before mutation, n is the residue number and $Xaa_2$ is the mutant amino acid. The abbreviation "Xaa" may be the three letter or single letter amino acid code. The amino acid residues for Hepatitis B virus DNA polymerase are numbered with the residue methionine in the motif Tyr Met Asp Asp (YMDD) (SEQ ID NO: 30) being residue number 550. In the priority document, Australian Patent Application No. PO3519, filed Nov. 8, 1996, the same methionine was designated residue 530. The amino acid residues for the DNA polymerase referred to in this specification have been re-numbered accordingly.

Hepatitis B Virus (HBV) can cause debilitating disease conditions and can lead to acute Liver failure. HBV is a DNA virus which replicates via an RNA intermediate and utilizes reverse transcription in its replication strategy (1). The HBV genome is of a computer nature having a partially double stranded DNA structure with overlapping open reading frames encoding surface, core, polymerase and X genes. The complex nature of the HBV genome is represented in FIG. 1.

The presence of an HBV DNA polymerase has led to the proposition that nucleoside analogues could act as effective anti-viral agents. Examples of nucleoside analogues currently being tested are penciclovir and its oral form famciclovir (2, 3, 4, 5) and lamivudine (6,7). There is potential for such agents to be used in the treatment of chronic HBV infection.

Peniciclovir has been recently shown to have potent inhibitory activity against duck HBV DNA synthesis in vitro and has been shown to inhibit HBV DNA polymerase-reverse transcriptase activity in vitro (8,9). Similarly, oral famiciclovir has been demonstrated to inhibit intra-hepatic replication of duck HBV virus in vivo (10). In man, famciclovir has been shown to reduce HBV DNA replication in a patient with severe hepatitis B following orthotopic liver transplantation (OLT) (11).

In work leading up to the present invention, nucleoside analogue antiviral therapy was used to control severe post-OLT recurrence of HBV infection (12). Long term therapy is mandatory where patients are immunosuppressed and the rate of HBV replication is very high. However, under such conditions, as with any long term chemotherapy of infectious agents, there is a potential for development of resistance or reduced sensitivity to the therapeutic agents employed.

In accordance with the present invention, the inventors have identified variants of HBV with mutations in the HBV DNA polymerase gene which to varying extents reduce the sensitivity of HBV to nucleoside analogues. The identification of these HBV variants is important for the development of assays to monitor nucleoside analogue therapeutic regimes and to screen for agents which can mask the effects of the mutation. In addition, since the HBV genome comprises a series of overlapping open reading frames, a nucleotide mutation in one open reading frame can affect translation products in another open reading frame. In further accordance with the present invention, the inventors have observed mutations which reduce the interactivity of immunological reagents, such as antibodies and immune cells, to viral surface components. Such viral variants are referred to herein as "escape mutants" since they potentially escape existing immunological memory.

Accordingly, one aspect of the present invention is directed to a variant of an isolated DNA virus which replicates via an RNA intermediate wherein said variant comprises a nucleotide mutation in a gene encoding a DNA polymerase resulting in at least one amino acid addition, substitution and/or deletion to said DNA polymerase.

Another aspect of the present invention provides a variant of an isolated DNA virus which replicates via an RNA intermediate wherein said variant comprises a nucleotide mutation in a gene encoding a viral surface component resulting in at least one amino acid addition, substitution and/or deletion in said viral surface component.

Still a further aspect of the present invention is directed to a variant of an isolated DNA virus which replicates via an RNA intermediate at least wherein said variant comprises a nucleotide mutation in an overlapping portion of at least two open reading frames resulting in an amino acid addition, substitution and/or deletion to translation products of said open reading frames.

Preferably, the DNA virus is a hepatitis virus or a related virus and is most preferably HBV.

A "related virus" in accordance with the present invention is one related at the genetic, immunological, epidemiological and/or biochemical levels.

Preferably, the mutation in the DNA polymerase results in decreased sensitivity of the HBV to a nucleoside analogue.

Preferably, the mutation in the viral surface component reduces the interactivity of immunological reagents such as antibodies and immune cells to the viral surface component.

Most preferably, the viral surface component is a viral surface antigen. The reduction in the interactivity of immunological reagents to a viral surface component generally includes the absence of immunological memory to recognise or substantially recognise the viral surface component.

A viral variant may, in accordance with a preferred aspect of the present invention, carry mutation only in the DNA polymerase or the surface antigen or may carry a mutation in both molecules. The term "mutation" is to be read in its broadest context and includes a silent mutation not substantially affecting the normal function of the DNA polymerase or surface antigen or may be an active mutation having the effect of inducing nucleoside analogue resistance or an escape mutant phenotype. Where multiple mutations occur in accordance with the present invention or where multiple phenotypes result from a single mutation, at least one mutation must be active or the virus must exhibit at least one altered phenotype such as nucleoside analogue resistance or reduced immunological interactivity to the surface antigen.

Regions of the HBV polymerase show amino acid similarity with other RNA-dependent DNA polymerases and RNA-dependent polymerases (13). In this specification, reference is made to the conserved regions defined by Poch et al (13) as domains B and C.

Preferably, the mutation results in an altered amino acid sequence in the B domain and/or C domain or regions proximal thereto of the HBV DNA polymerase. The present invention does not extend to a mutation alone in the YMDD (SEQ ID NO:30) motif of the C domain of the HBV DNA polymerase although such a mutation is contemplated by the present invention if it occurs in combination with one or more mutations in another location.

The mutation in the viral surface component is preferably in one or more amino acid residues within the major hydrophilic regions of the protein, in particular within the amino acid sequence 118–169 of the HBV viral surface antigen and also the regions from amino acids sequence 169 to 207 which are on the external surface of the protein.

Accordingly to a preferred aspect of the present invention, there is provided an HBV variant comprising a mutation in the nucleotide sequence encoding a DNA polymerase resulting in an amino acid addition, substitution and/or deletion in said DNA polymerase in its B domain and/or C domain or in a region proximal thereto, provided said mutation is not in the YMDD motif of the C domain alone, and wherein said variant exhibits decreased sensitivity to a nucleoside analogue.

Another preferred aspect of the present invention contemplates an HBV variant comprising a mutation in the nucleotide sequence encoding a viral surface component resulting in an amino acid addition, substitution and/or deletion in said viral surface component in a region corresponding to the B domain and/or C domain of HBV DNA polymerase or a region proximal to the B domain and/or C domain of HBV DNA polymerase and wherein said variant exhibits decreased interactivity of immunological reagents to said viral surface component.

Yet another preferred aspect of the present invention relates to an HBV variant comprising a mutation in the nucleotide sequence encoding a viral surface component resulting in an amino acid addition, substitution and/or addition in said viral surface component in a region defined by amino acids 118 to 169 and also 169 to 207 of the HBV surface antigen or functionally equivalent region wherein said variant exhibits decreased interactivity of immunological reagents to said viral surface component.

Still yet another aspect of the present invention is directed to an HBV variant comprising a mutation in an overlapping open reading frame in its genome wherein said mutation is in the B and/or C domain of DNA polymerase provided that it is not in the YMDD motif of the C domain alone; and in the overlapping region corresponding to amino acids 118 to 169 and also 169 to 207 or equivalent of HBV surface antigen and wherein said variant exhibits decreased sensitivity to a nucleotide analogue and exhibits decreased interactivity to immunological reagents specific to HBV surface antigens.

The viral variant exhibiting reduced interactivity to immunological reagents is an escape mutant since antibodies or other immunological response to HBV from a prior exposure to the virus or following vaccination are no longer effective in targeting a viral surface component since the mutation has altered a B- and/or T-cell epitope on the surface antigen.

The nucleoside analogues contemplated by the present invention include penciclovir and its oral form famciclovir as well as lamivudine (3TC). Different variants may be resistant to different nucleoside analogues. For example, in one embodiment, a variant in the B domain of HBV DNA polymerase may be resistant to famciclovir whereas a variant in the C domain may be resistant to 3TC.

The B domain is considered to comprise amino acid residues 505 to 529 of HBV DNA polymerase. This sequence is represented as follows: (SEQ ID NO:24)

S/A H PI I/V LGFRK I/L PMG V/G GLSPFLLAQF.

Reference to the B domain includes reference to proximal regions which includes up to about 20 amino acids on either side of the domain. Preferably, the mutation is in one or more of the following amino acids: (SEQ ID NO:25)

Q/K T Y/F G R/W KLHL Y/L S/A HPI I/V LGFRK I/L PMG V/G GLSPFLLAQFTSAI C/L S

The C domain comprises amino acids 546 to 556 as follows: (SEQ ID NO:26)

A/V F S/A YMDD V/L/M VLG

This includes the YMDD (SEQ ID NO:30) domain in which the methione residue is considered residue 550 (formally regarded as residue number 530). The residue numbering in this specification has been adjusted according to the new numbering system where the methione of YMDD is 550.

Reference to the C domain includes proximal regions of up to 20 amino acids either side of the domain.

The term "resistance" is used in its most general sense and includes total resistance or partial resistance or decreased sensitivity to a nucleoside analogue.

Preferably, the variants are in isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV.

Preferred mutations in the HBV DNA polymerase include one or more of Gly498Glu, Arg/Trp499Glu, Thr530Ser, Ile509Val, Phe512Leu, Val519Leu, Pro523Leu, Leu526Met, Ile533Leu, Met550Val/Ile and/or Ser559Thr. Preferred mutations in the HBV surface antigen include one or more of Asp144Glu and/or Gly145Arg. These correspond to positions 498 and 499 of DNA polymerase, respectively. More preferably, the variants contain two or more of the above-mentioned mutations.

One particular mutant HBV has the nucleotide sequence set forth in SEQ ID NO:17 and exhibits a multiphenotypic mutation rendering the DNA polymerase resistant to nucleoside analogues and an altered surface antigen such that it has reduced interactivity with antibodies to HBV surface antigen. The mutation is R/W499E in the DNA polymerase open reading frame as D144E and G145R in the surface antigen. This results from a double mutation in nucleotide numbers 226 and 227 of SEQ ID NO:17 to G and A. The polymerase protein of HBV is also similar to the DNA polymerase of Herpes Simplex Virus (HSV) (see FIG. 3 for alignment). A mutation (Gly841Cys) in the HSV polymerase gene was selected for in the presence of famciclovir (15). This mutation occurs in the same position as the G498E mutation of the HBV polymerase.

The present invention extends to the nucleotide sequence set forth in SEQ ID NO:17 as well as a nucleotide sequence having at least 60% similarity thereto and which carries a double mutation in the amino acid sequence of DNA polymerase and the HBV surface antigen. Accordingly, the present invention is directed to an HBV having the nucleotide sequence as set forth in SEQ ID NO:17 or a derivative thereof having a single of multiple nucleotide addition, substitution and/or deletion thereto such as a nucleotide sequence having at least 60% similarity to SEQ ID NO:17. A derivative includes parts, fragments, portions and homologues of SEQ ID NO:17. This aspect of the present invention also extends to a nucleotide sequence capable of hybridizing under low stringency conditions at 42° C. to SEQ ID NO:17.

Reference herein to a low stringency at 42° C. includes and encompasses from at least about 1% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions.

Accordingly, another aspect of the present invention contemplates a variant HBV exhibiting reduced sensitivity to a nucleoside analogue and reduced interactivity to an antibody to wild-type HBV surface antigen, said HBV variant characterised by one or more of the following characteristics:

(i) a nucleotide sequence of its genome as set forth in SEQ ID NO:17 or a sequence having at least 60% similarity thereto;

(ii) a nucleotide sequence capable of hybridising to SEQ ID NO:17 under low stringency conditions at 42° C.;

(iii) a mutation in an overlapping portion of open reading frames for DNA polymerization and HBV surface antigen; and (iv) a mutation in the B and/or C domain of HBV DNA polymerase and is a region corresponding to amino acids 118 to 169 and also 169 to 207 of HBV surface antigen.

According to another aspect of the present invention, there is provided a variant HBV comprising a nucleotide sequence which encodes a DNA polymerase having the amino acid sequence: (SEQ ID NO:27) and (SEQ ID NO:28)

$$X_1HPIX_2LGX_3RKX_4PMGX_5GLSX_6FLX_7AQFTSAX_8X_9$$

$$X_{10}FX_{11}YX_{12}DDX_{13}VLGAX_{14}X_{15}$$

wherein $X_1$ is S or A;
$X_2$ is I or V;
$X_3$ is F or L;
$X_4$ is I or L,
$X_5$ is L or V or G;
$X_6$ is P or L;
$X_7$ is L or M;
$X_8$ is I or L;
$X_9$ is C or L;
$X_{10}$ is A or V;
$X_{11}$ is S or A;
$X_{12}$ is M or I or V;
$X_{13}$ is V or L or M;
$X_{14}$ is K or R; and/or
$X_{15}$ S or T;

and wherein said variant exhibits reduced sensitivity to a nucleoside sensitivity to a nucleoside analogue, such as famciclovir (penciclovir) and/or lamivudine (3TC).

Another embodiment of the present invention is directed to a variant HBV comprising a nucleotide sequence which encodes a surface antigen having at least one amino acid substitution, addition and/or deletion to amino acid residue numbers 118 to 169 and also 169 to 207 of said surface antigen which corresponds to a DNA polymerase having the amino acid sequence: (SEQ ID NO:42) and (SEQ ID NO:43)

$$X_{16}TX_{17}X_{18}X_{19}KLHX_{20}X_{21}HPIX_{22}LGX_3RKX_4PMGX_5GLSX_6FLX_7AQFTSAX_8X_9$$

$$X_{10}FX_{11}YX_{12}DDX_{13}VLGAX_{14}X_{15}$$

wherein:

$X_{16}$ is Q or K;
$X_{17}$ is Y or F;
$X_{18}$ is G or E;
$X_{19}$ is R or W or E;
$X_{20}$ is Y or L;
$X_{21}$ is S or A;
$X_{22}$ is I or V;
$X_3$ is F or L;
$X_4$ is I or L;
$X_5$ is L or V or G;
$X_6$ is P or L;
$X_7$ is L or M;
$X_8$ is I or L;
$X_9$ is C or L;
$X_{10}$ is A or V;
$X_{11}$ is S or A;
$X_{12}$ is M or I or V;
$X_{13}$ is V or L or M;
$X_{14}$ is K or R; and/or
$X_{15}$ S or T;

and wherein said variant exhibits reduced interactivity with immunological reagents, such as an antibody, to said surface antigen.

Figure 6:
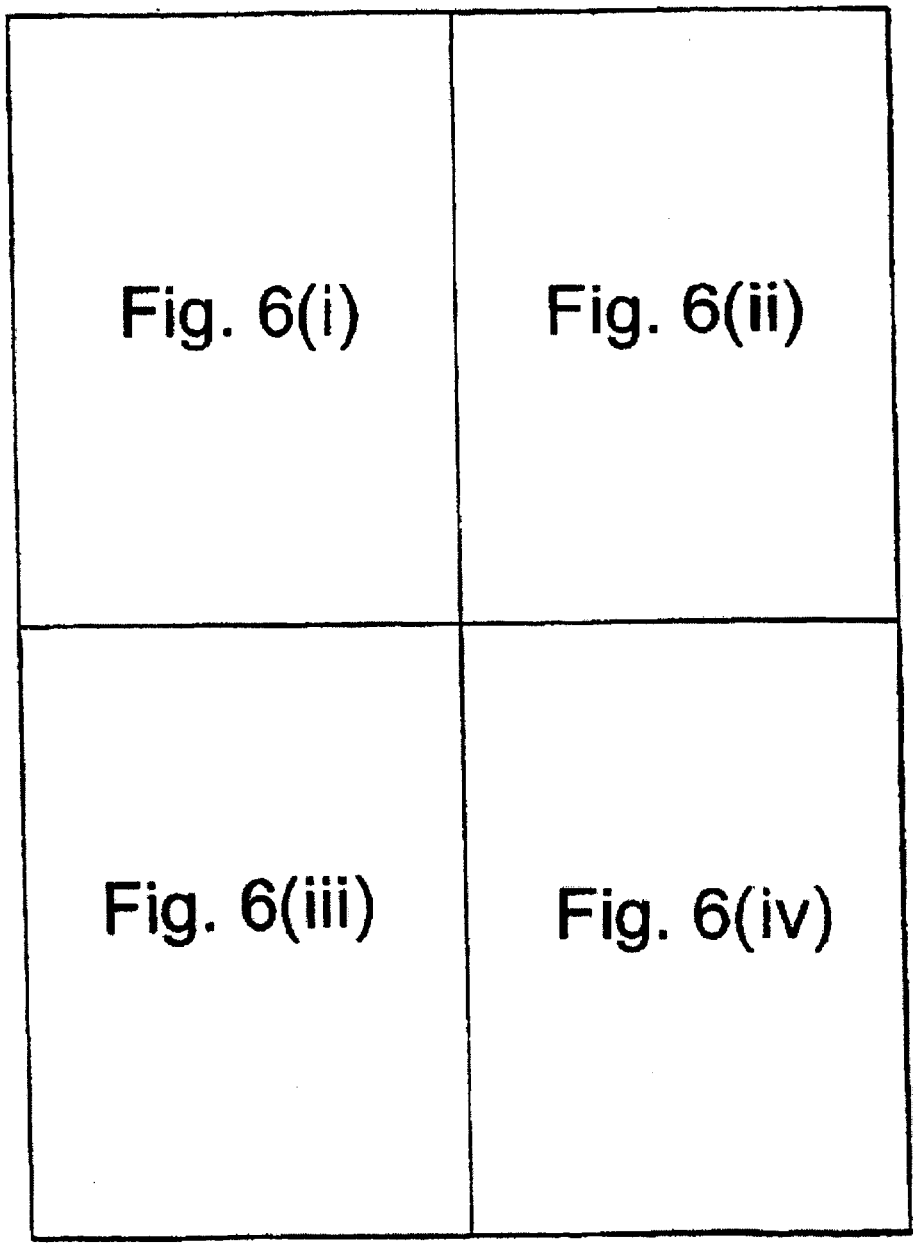

Examples of preferred variants comprise the amino acid sequences shown in FIG. 4. An example of a particularly preferred mutant is shown in FIG. 6 (SEQ ID NO:17).

The identification of the variants of the present invention permits the generation of a range of assays to detect such variants. The detection of such variants may be important in identifying resistant variants to determine the appropriate form of chemotherapy and/or to monitor vaccination protocols.

Accordingly, another aspect of the present invention contemplates a method for determining the potential for an HBV to exhibit reduced sensitivity to a nucleoside analogue, said method comprising isolating DNA or corresponding mRNA from said HBV and screening for a mutation in the nucleotide sequence encoding HBV DNA polymerase resulting in at least one amino acid substitution, deletion and/or addition in the B domain or C domain or a region proximal thereto of said DNA polymerase wherein the presence of such a mutation is an indication of the likelihood of resistance to said nucleoside analogue.

A further aspect of the present invention provides a method for determining the potential for an HBV to exhibit reduced interactivity to antibody to HBV surface antigen, said method comprising isolating DNA or corresponding mRNA from said HBV and screening for a mutation in the nucleotide sequence encoding HBV surface nitrogen resulting in at least one amino acid substitution, deletion and/or addition in amino acids 118 to 169 and/or 169 to 207 of said surface antigen or a region proximal thereto of said surface antigen wherein the presence of such a mutation is an indication of the likelihood of reducing interactivity of said antibodies to said mutated surface antigen.

Preferably, the assay determines a mutation resulting in a Glu/Val519Leu substitution and/or a Leu526Met substitution and/or a Pro523Leu substitution and/or a Ser559Thr substitution, and/or Gly498Glu substitution, and/or Arg/Trp496Glu substitution.

The DNA or corresponding RNA may be assayed or alternatively the DNA polymerase or surface antigen may be screened for the mutation.

The detection according to this aspect of the invention may be any nucleic acid-based detection means, for example nucleic acid hybridisation techniques or polymerase chain reaction (PCR). The invention further encompasses the use of different assay formats of said nucleic acid-based detection means, including restriction fragment length polymorphism (RFLP), amplified fragment length polymorphism (AFLP), single-strand chain polymorphism (SSCP), amplification and mismatch detection (AMD), interspersed repetitive sequence polymerase chain reaction (LRS-PCR), inverse polymerase chain reaction (iPCR) and reverse transcription polymerase chain reaction (RT-PCR), amongst others.

The present invention extends to a range of immunological based assays to detect variant HBV DNA polymerase or surface antigen. These assays are based on antibodies directed to naturally occurring HBV DNA polymerase or surface antigen which do not, or substantially do not, interact with the variant HBV DNA polymerase or surface antigen. Alternatively, antibodies to a variant HBV DNA polymerase or surface antigen are used which do not or substantially do not, interact with naturally occurring HBV DNA polymerase or surface antigen.

Monoclonal or polyclonal antibodies may be used although monoclonal antibodies are preferred as they can be produced in large quantity and in a homogenous form. A wide range of immunoassay techniques are available such as described in U.S. Pat. Nos. 4,016,043, 4,424,279 and 4,018,653.

The detection of amino acid variants of DNA polymerase is conveniently accomplished by reference to the consensus amino acid sequence shown in FIG. 4. The polymorphisms shown represent the variations shown in various data bases for active pathogenic HBV strains. Where an HBV variant comprises an amino acid different to what is represented, then such an isolate is considered a putative HBV variant having an altered DNA polymerase activity.

Accordingly, another aspect of the present invention contemplates a method for determining whether an HBV isolate encodes a variant DNA polymerase, said method comprising determining the amino acid sequence of its DNA polymerase directly or via a nucleotide sequence and comparing same to the amino acid sequence below: (SEQ ID NO:29)

```
          DOMAIN A
421       430        440        450
SNDLSWLSLD VSAAPYHIPPL HPARMPWLLIVGSSGLSDRYVA
460            470             480          490
RLSSTNSRNNI*N  NYHQKYGR***DNLH  DNSYCSRNQLYVS LLMLLYKQTYPGRW
                DOMAIN B
500          510          520         530
KLHLYLSANPIIVLGFRKILPMGVG GLSPFLGAOF TSAICLASVMVTRCR
                DOMAIN C
540            550            560
AFVPHCLVAVFSAY MDDALMVLGAXRST VGQRRLSREC PLFYTAAS

                DOMAIN D          DOMAIN E
570             580          590          600
VITCNSFVLLSDLVGI KLNPWQKTGRW  GYSLNFHCYVII G
```

where the presence of a different amino acid from the consensus sequence indicates a putative HBV variant.

The present invention further contemplates agents which mask the nucleoside analogue resistance mutation. Such agents will be particularly useful in long term treatment by nucleoside analogues. The agents may be DNA or RNA or proteinaceous or non-proteinaceous chemical molecules. Natural product screening such as from plants, coral and microorganisms is also contemplated as a useful potential source of masking agents. The agents may be in isolated form or in the form of a pharmaceutical composition and may be administered sequentially or simultaneously with the nucleoside analogue.

The subject invention extends to kits for assays for variant HBV. Such kits may, for example, contain the reagents from PCR or other nucleic acid hybridisation technology or reagents for immunologically based detection techniques.

The present invention is further described by the following non-limiting figures and examples.

In the figures:

FIG. 1 is a diagrammatic representation showing the partially double stranded DNA HBV genome showing the overlapping open reading frames encoding surface (S), core (C), polymerase (P) and X gene.

Figure 2:
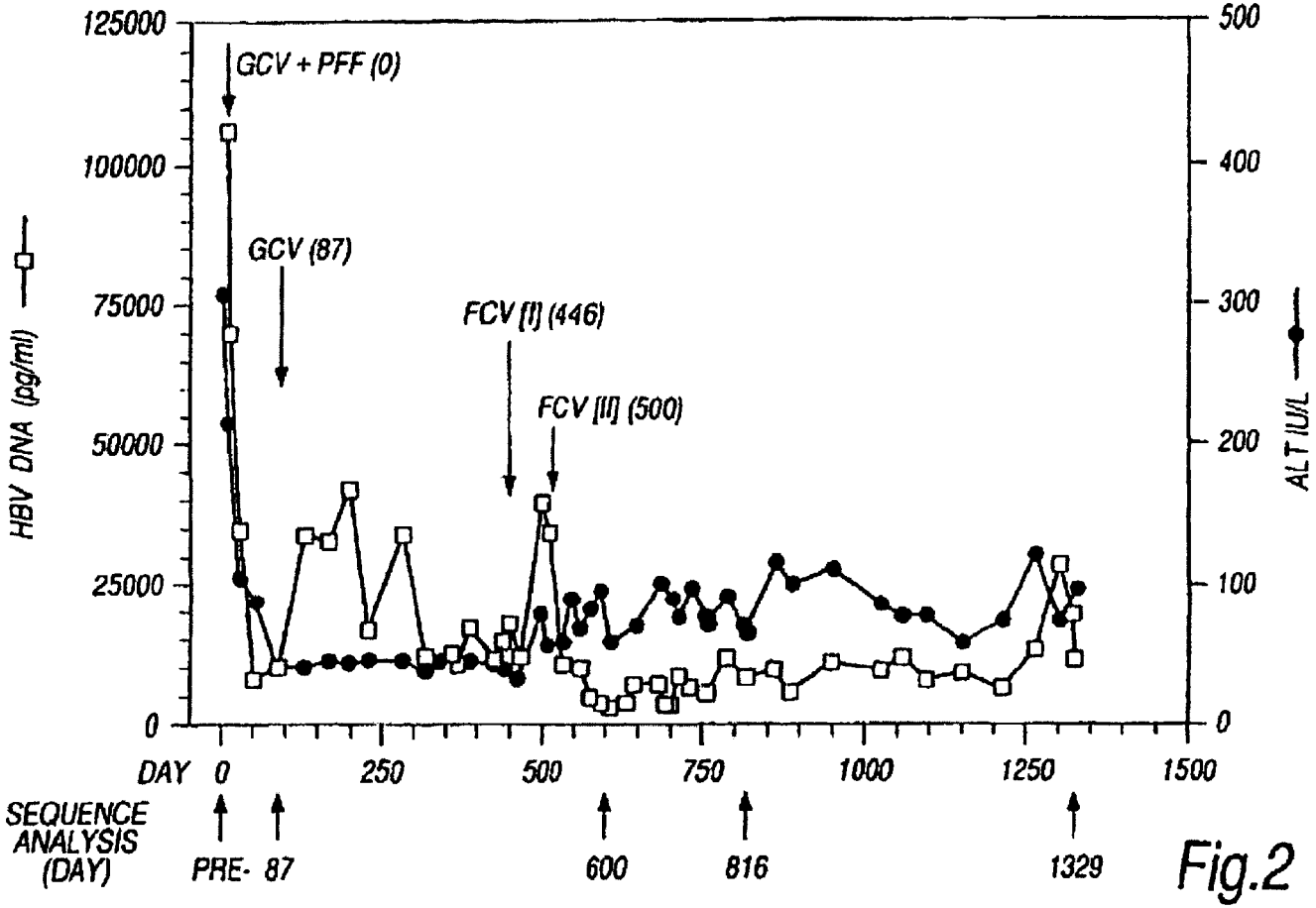

FIG. 2 is a graphical representation showing serum biochemical (ALT) and virological (HBV DNA) profile in the transplant patient and the responses following the introduction of various antiviral treatment programs. Treatment GCV+PFF, GCV and FCV[I] and FCV[II] are described in detail in the examples. Treatment GCV+PFF is ganciclovir plus foscarnet combination (12), treatment GCV is parenteral ganciclovir maintenance therapy and treatment FCV[I] and FCV[II] is oral famciclovir therapy at a dose of 250 mg or 500 mg twice daily, respectively. The day each therapy commenced is shown in brackets. The ALT (•—•) and the HBV DNA (□—□) responses are plotted against time from the commencement of antiviral therapy at 6 months post-OLT. The five key time points for the sequence analysis, pre-treatment (PRE-) and days 87, 600, 816 and 1329 post antiviral treatment are shown.

FIG. 3 is a representation showing amino acid alignment of the RNA dependent DNA polymerase sequence motifs from HBV, pre-treatment with famciclovir and 370 days post-treatment (total antiviral therapy of 816 days), with the woodchuck hepatitis virus (WHV), human immunodeficiency virus (HIV), and the comparable regions with the DNA polymerase of herpes simplex virus (HSV) (13, 14) (SEQ ID NO:30–37). The conserved asparagine (D) and glycine (G) residues within the polymerase motifs are in bold type and the amino acid changes found after famciclovir treatment are in bold type and underlined. The location of the mutated amino acid residues within HSV polymerase are shown. The bold face underlined glycine (G) residue in the IISV polymerase becomes a cysteine (C) during penciclovir treatment (15).

FIG. 4 is a representation showing conserved regions of domain A to E (underlined) of HBV. M in YMDD is designated amino acid number 550. * indicates greater than three amino acid possibilities at this position of the consensus sequence (SEQ ID NO:29).

FIG. 5 is a representation showing amino acid alignment of the RNA dependent DNA polymerase sequence motifs from HBV, noting the amino acid changes which have been selected for in the presence of famciclovir and 3TC (SEQ ID NOS:36–41 and SEQ ID NOS:45–49). HBV concensus sequence was derived from published sequences in Genebank/Entrez. The conserved asparagine (D) and glycine (G) residues within the polymerase motifs are in bold type. The amino acid changes found after famciclovir treatment are in bold green type and underlined and after 3TC are in bold blue type and are underlined. The amino acid sequence of the HBV isolated from patient A and patient B, during famciclovir treatment and from Patient C who did not respond to famciclovir and was later treated with 3TC and, in which a resistance mutation was selected (3TC 2). The published 3TC changes detected by Ling et al (16) is shown in 3TC 1.

FIG. 6 is a representation showing the nucleotide sequence of an HBV variant (SEQ ID NO:17) and corresponding amino acid sequences for HBV DNA polymerase (SEQ ID NO:18) and HBV surface antigen (SEQ ID NO:19) showing in bold mutations R/W499 in the polymerase and D144E and G145R in the surface antigen.

EXAMPLE 1

Case Study

1. Patient A

The inventors sequenced the HBV polymerase and X open reading frames from a series of isolates from a patient who received antiviral therapy for almost 4 years following post liver transplant recurrence of HBV infection (FIG. 2).

The patient (male, aged 42 years) was transplanted because of end-stage liver failure due to chronic HBV infection. The initial post transplant course was unremarkable but by 5 months there was evidence of recurrent infection and very high levels of viral replication and deteriorating liver function (12). The histological picture was consistent with fibrosing cholestatic hepatitis. Antiviral treatment was commenced approximately 6 months post-OLT. Initially, the patient received intravenous (iv) ganciclovir (GCV; 10 mg/kg/day) in combination with iv foscarnet (PFF; 50–125 mg/kg/day; the dose depending on renal function) (12). This is the treatment of GCV+PFF described in FIG. 2 which lasted for 86 days. Maintenance iv GCV (3.3–6.7 mg/kg/day) three times per week was commenced on day 87 of antiviral treatment (GCV in FIG. 2). Oral famciclovir (250 mg, twice daily) was commenced on day 446 of therapy (FCV [I] in FIG. 2) which was increased to 500 mg twice daily (FCV [II] in FIG. 1) on day 500. The patient is currently on this treatment regime. The clinical and virological details of this patient preceding famciclovir therapy have been reported (12).

Serum samples were routinely collected and stored at −70° C. Informed consent was obtained from the patient to use these samples for research purposes. FIG. 2 shows the alanine amino transferase (ALT) and HBV DNA levels over the entire course of antiviral treatment. The 5 samples chosen for additional studies cover a period of almost four years.

2. Patient B

Patient B

Patient B was retransplanted for pre-core mutant associated HBV-related allograph loss 14 months after the initial liver transplant. Antiviral treatment with GCV (7.5 mg/kg/day) was given for 10 months and then ceased. This was followed by oral famciclovir therapy given (500 mg 3 times/day).

From patient B the entire HBV polymerase gene was sequenced from a serum HBV sample taken post-transplantation after 850 days FCV therapy. The regions encompassing the catalytic domains of the HBV polymerase were sequenced from a serum sample pretransplant prior to FCV treatment.

3. Patient C

This patient did not respond to famciclovir and was later treated with lamivudine (3TC) (6,7) in which a resistance mutation was selected.

4. Patient D

This patient is treated with famciclovir in which resistance mutation is selected.

EXAMPLE 2

Viral Markers in Serum

Hepatitis B surface antigen (HbsAg), hepatitis B e antigen (HbeAg), anti-HBe, hepatitis B core antigen (HbcAg) specific IgG and IgM, hepatitis A specific IgM, hepatitis delta antigen and antibody, and anti-hepatitis C virus antibody were measured using commercially available immunoassays (Abbott Laboratories, North Chicago, Ill.). Only the HBV markers were positive. Hepatitis B viral DNA levels were measured and quantified using a capture hybridisation assay according to the manufacturer's directions (Digene Diagnostics Inc., Beltsville, Md.). This patient was infected with a pre-core HBV mutant pre-OLT (12) and this status did not change post-OLT.

EXAMPLE 3

Sequencing and Cloning of HBV DNA

1. Extraction of DNA from sera: Aliquots of 50 μl of sera were mixed with 150 μl TE (10 mmol/L Tris-HCl (pH 7.5), 2 mmol/L EDTA), 1% w/v sodium dodecyl sulfate and 1 mg/ml pronase and incubated at 37° C. for 2 hours. DNA was deproteinised by phenol/chloroform, precipitated with isopropanol and dissolved in 25 μl nuclease-free water.

2. Amplification of the viral polymerase and X genes by polymerase chain reaction (PCR): Oligonucleotides were synthesised by Bresatec, Adelaide, Australia. For amplification of the polymerase gene, the sense primer was 5'-GGA GTG TGG ATT CGC ACT CC-3' [SEQ ID NO:1] (nucleotides [nt] −40 to −21) and the antisense primer was 5'-GCT CCA AAT TCT TTA TA-3' [SEQ ID NO:2] (nt 2831 to 2847). For amplification of the X gene, the sense primer was 5'-CCT TTA CCC CGT TGC CCG GC-3' [SEQ ID NO:3] (nt 2055 to 2074) and the antisense primer 5'-GCT CCA AAT TCT TTA TA-3' [SEQ ID NO:4] (nt 2831 to 2847). All nt are numbered from the start of the polymerase gene. Each reaction was carried out using 5 μl of the extracted DNA as template, 1.5 U of Taq polymerase (Perkin Elmer Cetus, Norwalk, Conn.), 1 μmol/L of sense and antisense primers, 200 μmol/L each of deoxynucleoside triphosphates, 50 mmol/L Kcl, 3.5 mmol/L MgCl, 10 mmol/L Tris-Hcl (pH 8.3) and 0.01 % w/v gelatin. Amplification was achieved by 40 cycles of denaturation (94° C. for 1 min), annealing (55° C. for 1 min) and extension (72° C. for 1.5 min), followed by a final extension of 7 min (Perkin-Elmer Cetus, Norwalk, Conn.). The PCR product was analysed by gel electrophoresis through 1.5% w/v agarose and visualised by UV irradiation after staining with ethidium bromide.

3. Sequencing of the polymerase and X genes of HBV DNA: The specific amplified product was purified using Geneclean II (BIO 101 Inc., La Jolla, Calif.) and directly sequenced using Sequenase version 2.0 (United States Biochemical Corp., Cleveland, Ohio). The PCR primers were used as sequencing primers and internal primers were additionally synthesised to sequence the internal regions of the PCR products. The following internal and sequencing primers were used 5'-GCC GCG TCG CAG AAG ATC TCA AT-3' [SEQ ID NO:5] (nt 104–126), 5'-GGT TCT ATC CTA ACC TTA CC-3' [SEQ ID NO:6] (nt 341–360), 5'-GCC TCA TTT TGT GGG TCA CCA TA-3' [SEQ ID NO:7] (nt 496–518), 5'-TGG GGG TGG AGC CCT CAG GCT-3' [SEQ ID NO:8] (nt 731–751), 5'-CAC AAC ATT CCA CCA AGC TC-3' [SEQ ID NO:9] (nt 879–899), 5'-AAA TTC GCA GTC CCC AAC-3' [SEQ ID NO:10] (nt 1183–1195), 5'-GTT TCC CTC TTC TTG CTG T-3' [SEQ ID NO:11] (nt 1429–1447), 5'-TTT TCT TTT GTC TTT GGG TAT-3' [SEQ ID NO:12] (nt 1683–1703) 5'-CCA ACT TAC AAG GCC TTT CTG-3' [SEQ ID NO:13] (nt 1978–1999), 5'-CAT CGT TTC CAT GGC TGC TAG GC-3' [SEQ ID NO:14] (nt 2239–2262).

4. Cloning of the HBV polymerase gene into pUC18: Due to the small amount of HBV DNA in the samples, the region encompassing nt 1429 to 1703 from the HTBV polymerase gene were amplified by PCR using the primers-5'-GTT TCC CTC TTC TTG CTG T-3' [SEQ ID NO:15] (nt 1429–1447) and 5' ATA CCC AAA GAC AAA AGA AAA-3' [SEQ ID NO:16] (nt 1703–1683), before cloning. The DNA was purified with Geneclean II and ligated using T4 DNA ligase (New England Biolabs, Beverly, Mass.) into a Sma I-digested dephosphorylated pUC18 plasmid (Pharmacia Biotech, NJ). Clones were directly sequence as above.

EXAMPLE 4

DNA Polymerase Assay

Samples of serum (100 μl) were applied to a 20% w/v sucrose cushion in TNE (20 mmol/L Tris-HCl pH 7.4, 150 mmol/L $NaCl_2$ 1 mmol/L EDTA) and centrifuged at 200,000 g for 3 hr at 10° C. using an SW41 rotor in a Beckman Model L8 ultracentrifugc. The pellet was resuspended in 50 mmol/L TRIS-HCl pH 7.5 containing 1.5% v/v Triton-X100, 100 mmol/L Kcl and 0.01% v/v 2-mercaptoethanol and allowed to stand overnight at 4° C. Small aliquots of the suspension were assayed for endogenous HBV DNA polymerase activity essentially as described by Price et al (16). Each assay was performed in a total volume of 30 μl which contained 20 μl of the partly purified HBV and (final concentrations) 30 mmol/L Tris-HCl pH 7.5, 30 mmol/L $MgCl_2$, 10 μmol/L each dATP, dTTP and dGTP, and 0.01 μM [$\alpha$-$^{32}$P]-dCTP (3,000 Ci/mmol) (Dupont NEN, Boston, Mass.). To test for penciclovir triphosphate (PCV-TP) sensitivity, paired assays were performed on each sample, with an excess (100 μmol/L penciclovir-triphosphate included in the reaction mixture in one assay of each pair. After 2 hr at 37° C., reactions were stopped by spotting 20 μl aliquots of each reaction mix onto 25 mm diameter glass fibre discs (Advantex, Tokyo, Japan) which had been presoaked in 10% w/v trichloroacetic acid (TCA). Discs were dried before washing in ice-cold 10% w/v TCA containing 10 mmol/L sodium pyrophosphate.

Three further 10 min. washes in cold 5% v/v TCA followed. The washed discs were finally rinsed in absolute ethanol, air dried, and counted for radioactivity. Inhibition of HBV DNA polymerase activity by PCV-TP was expressed as the percentage difference in activity in the assay mix containing PCV-TP compared to the matched control. Because of limited sample amounts, it was not possible to standardize enzyme activity or to perform replicate assays. Despite the inherent variability of the assay, a general time related decrease in sensitivity of the HBV DNA polymerase to PCV-TP was evident (see Table 1).

EXAMPLE 5

Effect of Antiviral Therapy

Upon commencement of the antiviral treatment strategy GCV+PFF, the level of HBV DNA post-OLT decreased from over 100,000 pg/ml to 10,800 pg/ml by day 87 (FIG. 1). This reduction in viraemia was associated with clinical, biochemical and histological improvement (12). Maintenance famciclovir therapy (treatment GCV) resulted in fluctuating levels of HBV DNA over the ensuring 359 days with two peaks of HBV DNA observed. The switch to oral famciclovir on day 446 was also associated with a rise in HBV DNA, but this was likely to have been the result of insufficient dosing (FCV[I] in FIG. 2) rather than a breakthrough in treatment. Following dose increase to FCV[II] on day 500, there was a decrease in HBV DNA. However, the level of HBV DNA gradually rose over time from 3,000 pg/ml on day 600 (154 days of famciclovir), to 8,800 pg/ml on day 816 (370 days famciclovir), peaking at 29,000 pg/ml on day 1302 (856 days of famciclovir), then stabilising at around 12,000 pg/ml on day 1329 (883 days of famciclovir). A students test of the DNA levels during the treatment period from days 816 to days 1329, revealed statistically significant rise. There was a 1.5 to 2 fold rise in ALT levels over the same time interval (FIG. 2) and no change in clinical status.

EXAMPLE 6

Nucleotide Changes

The X and the polymerase genes of HBV were sequenced at five time points (FIG. 2). During almost 4 years of the antiviral therapy there were no changes in the X gene compared to the pretreatment sequence. However, there were 5 nt changes detected in the polymerase gene from day 816 and day 1329 samples (Table 1). These changes were detected in separate independent PCR amplifications; furthermore the mutations were detected by sequencing both strands and are therefore unlikely to be the result of PCR generated errors. The nt changes in the polymerase gene were first detected after 816 days of treatment, when the patient had been treated with famciclovir for 370 days. However, only two nt changes, at positions 1498 and 1519 resulted in amino acid changes, Val 519-Leu and Leu 526-Met, respectively. These two nt changes appeared concurrently. At 816 days, three different nt (C,G,T) were detected at position 1498 (all of which would result in a Val to Leu change). After 1329 days post-treatment, thymidine was the dominant species at nt 1498. The amino acid changes at 816 and 1329 days post treatment coincided with reduced scrum HBV DNA polymerase sensitivity to PCV-TP (Table 1). These nt changes were not found in 6 patients with post-OLT recurrent HBV infection who were not undergoing FCV therapy.

The region encompassing the nt mutations which gave rise to amino acid changes from the sample taken at 1329 days was cloned and sequenced. Three quasi-species were detected. Seventy-five percent (15/20) of the clones contained both the 1498 and 1519 mutations which occurred together. Pretreatment non-mutated sequences were detected in 3/20 of the clones. A further mutation at nt 1511, which would result in a proline to leucine change at position 523, was detected in 2/20 of the clones. This mutation was not detected with the two dominant mutations, 1498 (Val 519-Leu) and 1519 (Leu 526-Met), nor was it detected by direct PCR sequencing, indicating it probably occurs at a low frequency. Viral DNA from the sample obtained at 600 days (150 days of FCV treatment) was also cloned and sequenced; however, only the pre-treatment sequences were detected.

EXAMPLE 7

Nucleotide Changes in Patents B, C and D

The amino acid changes in HBV isolated from patients B and C are shown in FIG. 5, and from patient D is shown in FIG. 6. In FIG. 5, patient A is the same as shown in FIG. 3.

Patient B was undergoing long term famciclovir treatment (>850 days). The amino acid change selected during famciclovir treatment is shown as HBV (patient B) in FIG. 5. Patient C did not respond to famciclovir and was later treated with 3TC (lamivudine [6,7]). The HBV isolated during FCV treatment from patient C, is shown as HBV (patient C-FCV). All 3TC resistance mutations which developed during treatment with 3TC is shown as HBV (patient C-3TC). The sequence analysis showed a mutation (Thr-Ser substitution) in the HBV polymerase gene near the C domain but no mutation was initially detected in the YMDD motif. A mutation of Met 550 to Ile in the YMDD motif was detected from HBV isolated 32 days (333 days post treatment) after the HBV containing the Thr-Ser substitution was isolated.

EXAMPLE 8

Escape Mutants

Using the method hereinbefore described, HBV variants are screened for escape mutations. These are mutations in surface components such as the HBV surface antigen which reduce the interactivity of the surface component to antibodies or other immunological reagents. Given the overlapping open reading frame of HBV genome, a single mutation may have multiphenotypic consequences. For example, a mutation in the HBV DNA polymerase may also have an affect on the HBV surface antigen.

Preferred mutations in the HBV surface antigen are in amino acids 118 to 169 and/or 169 to 207 such as D144E or G145R. These correspond to DNA polymerase mutations G498E and V499L.

A particularly preferred escape mutant and nucleoside analogue resistant mutant has a nucleotide sequence set forth in FIG. 6 with corresponding amino acid sequences for the DNA polymerase and surface antigen.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

| | | Nucleotide mutations in the polymerase gene and the resulting amino acid changes during antiviral therapy | | | | | | |
|---|---|---|---|---|---|---|---|---|
| Days of antiviral treatment | Days post famciclovir treatment | POLYMERASE GENE | | | | | | Institution of HBV DNA Polymerase by PCV-TP[++] |
| | | nt 297 | nt 1458 | nt 1511[+] | nt 1519 | nt 2005 | nt 2331 | |
| Pretreatment | NR[+++] | T | G | C | C | C | G | 40% |
| 87 | NR | — | — | — | — | — | — | NA[++++] |
| 600 | 154 | — | — | — | — | — | — | 30% |
| 816 | 370 | — | G,T,C | — | A | — | — | 0% |
| 1329 | 883 | C | T | T | A | A | A | 0% |
| Amino acid change | | None | Val 519-Leu | Pro 523-Leu | Leu 526-Met | None | None | |

The dashes indicate no change from the pre-treatment nucleotide.

[+]The mutation was only detected after cloning the PCR product after 1329 days of antiviral treatment. It occured as a low frequency and was present in only 10% of clones.

[++]The percentage inhibition of HBV DNA polymerase by PCV-TP in the viro assay as described in the Methods action.

[+++]NR—not relevant

[++++]NA—not accessible

BIBLIOGRAPHY

1. Summers J, Mason W. Cell (1982) 29: 403–415.
2. Vere Hodge R. A. Antiviral Chem Chemother (1993) 4:67–84.
3. Boyd M R et al Antiviral Chem Chemother. (1987) 32: 358–363.
4. Kruger T et al Hepatology (1994) 22: 219A.
5. Main J et al. J. Viral Hepatitis (1996) 3:211–215.
6. Severini A et al Antimicrobial Agents Chemother (1995) 39: 1430–1435.
7. Dienstag J L et al New England J Med (1995) 333: 1657–1661.
8. Shaw T, et al. Antimicrobial Agents Chemother (1994) 38:719–723.
9. Shaw T, et al. Hepatology (1996) 24: in press.
10. Tsiquaye K N, et al. J. Med Virol (1994) 42: 306–310.
11. Boker K H W, et al. Transplantation (1994) 57: 1706–1708.
12. Angus P, et al. J. Gastroenterol Hepatol (1993) 8: 353–357.
13. Poch O, et al. EMBO J. (1989) 8: 3867–3874.
14. Delarue M, et al. Protein Engineering (1990) 3: 461–467.
15. Chiou H C, et al. Antiviral Chem Chemother (1995) 6: 281–288.
16. Ling R, et al. Hepatology (1996) 24: 711–713.
17. Price P M, et al. Hepatology 1992 16: 8–13.

SEQUENCE LISTING

```
<160> NUMBER OF SEQ ID NOS: 57

<210> SEQ ID NO 1
<211> LENGTH: 20
<212> TYPE: DNA
<213> ORGANISM: Hepatitis B virus

<400> SEQUENCE: 1

ggagtgtgga ttcgcactcc                                                20


<210> SEQ ID NO 2
<211> LENGTH: 17
<212> TYPE: DNA
<213> ORGANISM: Hepatitis B virus

<400> SEQUENCE: 2

gctccaaatt ctttata                                                   17


<210> SEQ ID NO 3
<211> LENGTH: 20
<212> TYPE: DNA
<213> ORGANISM: Hepatitis B virus

<400> SEQUENCE: 3

cctttacccc gttgcccggc                                                20


<210> SEQ ID NO 4
<211> LENGTH: 17
<212> TYPE: DNA
<213> ORGANISM: Hepatitis B virus

<400> SEQUENCE: 4

gctccaaatt ctttata                                                   17


<210> SEQ ID NO 5
<211> LENGTH: 23
<212> TYPE: DNA
<213> ORGANISM: Hepatitis B virus

<400> SEQUENCE: 5

gccgcgtcgc agaagatctc aat                                            23


<210> SEQ ID NO 6
<211> LENGTH: 20
<212> TYPE: DNA
<213> ORGANISM: Hepatitis B virus
```

-continued

<400> SEQUENCE: 6 ggttctatcc taaccttacc 20

<210> SEQ ID NO 7
<211> LENGTH: 23
<212> TYPE: DNA
<213> ORGANISM: Hepatitis B virus

<400> SEQUENCE: 7 gcctcatttt gtgggtcacc ata 23

<210> SEQ ID NO 8
<211> LENGTH: 21
<212> TYPE: DNA
<213> ORGANISM: Hepatitis B virus

<400> SEQUENCE: 8 tgggggtgga gccctcaggc t 21

<210> SEQ ID NO 9
<211> LENGTH: 20
<212> TYPE: DNA
<213> ORGANISM: Hepatitis B virus

<400> SEQUENCE: 9 cacaacattc caccaagctc 20

<210> SEQ ID NO 10
<211> LENGTH: 18
<212> TYPE: DNA
<213> ORGANISM: Hepatitis B virus

<400> SEQUENCE: 10 aaattcgcag tccccaac 18

<210> SEQ ID NO 11
<211> LENGTH: 19
<212> TYPE: DNA
<213> ORGANISM: Hepatitis B virus

<400> SEQUENCE: 11 gtttccctct tcttgctgt 19

<210> SEQ ID NO 12
<211> LENGTH: 21
<212> TYPE: DNA
<213> ORGANISM: Hepatitis B virus

<400> SEQUENCE: 12 ttttcttttg tctttgggta t 21

<210> SEQ ID NO 13
<211> LENGTH: 21
<212> TYPE: DNA
<213> ORGANISM: Hepatitis B virus

<400> SEQUENCE: 13 ccaacttaca aggcctttct g 21

<210> SEQ ID NO 14
<211> LENGTH: 23
<212> TYPE: DNA
<213> ORGANISM: Hepatitis B virus -continued

<400> SEQUENCE: 14 catcgtttcc atggctgcta ggc 23

<210> SEQ ID NO 15
<211> LENGTH: 19
<212> TYPE: DNA
<213> ORGANISM: Hepatitis B virus

<400> SEQUENCE: 15 gtttccctct tcttgctgt 19

<210> SEQ ID NO 16
<211> LENGTH: 21
<212> TYPE: DNA
<213> ORGANISM: Hepatitis B virus

<400> SEQUENCE: 16 atacccaaag acaaaagaaa a 21

<210> SEQ ID NO 17
<211> LENGTH: 550
<212> TYPE: DNA
<213> ORGANISM: Hepatitis B virus
<220> FEATURE:
<221> NAME/KEY: CDS
<222> LOCATION: (1)..(549)

<400> SEQUENCE: 17

```
tct tcc aat ttg tcc tgg tta tcg ctg gat gtg tct gcg gcg ttt tat      48
Ser Ser Asn Leu Ser Trp Leu Ser Leu Asp Val Ser Ala Ala Phe Tyr
  1               5                  10                  15

cat att cct ctt cat cct gct gct atg cct cat ctt ctt att ggt tct      96
His Ile Pro Leu His Pro Ala Ala Met Pro His Leu Leu Ile Gly Ser
             20                  25                  30

tct gga tta tca agg tat gtt gcc cgt ttg tcc tct aat tcc agg atc     144
Ser Gly Leu Ser Arg Tyr Val Ala Arg Leu Ser Ser Asn Ser Arg Ile
         35                  40                  45

aac aac aac atg caa aac ctg cac gac tcc tgc tca agg caa ctc tac     192
Asn Asn Asn Met Gln Asn Leu His Asp Ser Cys Ser Arg Gln Leu Tyr
     50                  55                  60

gtt tcc ctc atg ttg ctg tac aaa acc tac gga gag aaa ttg cac ctg     240
Val Ser Leu Met Leu Leu Tyr Lys Thr Tyr Gly Glu Lys Leu His Leu
 65                  70                  75                  80

tat tcc cat ccc atc gtc ctg ggc ttt cgc aaa ata cct atg gga gtg     288
Tyr Ser His Pro Ile Val Leu Gly Phe Arg Lys Ile Pro Met Gly Val
                 85                  90                  95

ggc ctc agt ccg ttt ctc ttg gct cag ttt act agt gcc att tgt tca     336
Gly Leu Ser Pro Phe Leu Leu Ala Gln Phe Thr Ser Ala Ile Cys Ser
            100                 105                 110

gtg gtt cgt agg gct ttc ccc cac tgt ttg gct ttc agc tat atg gat     384
Val Val Arg Arg Ala Phe Pro His Cys Leu Ala Phe Ser Tyr Met Asp
        115                 120                 125

gat gtg gta ttg ggg gcc aag tct gta cag cat cgt gag gcc ctt tat     432
Asp Val Val Leu Gly Ala Lys Ser Val Gln His Arg Glu Ala Leu Tyr
    130                 135                 140

acc gct gtt acc aat ttt ctt ttg tct ctg ggt ata cat tta aac cct     480
Thr Ala Val Thr Asn Phe Leu Leu Ser Leu Gly Ile His Leu Asn Pro
145                 150                 155                 160

aac aaa aca aaa aga tgg ggt tat tcc cta aac ttc atg ggt tac ata     528
Asn Lys Thr Lys Arg Trp Gly Tyr Ser Leu Asn Phe Met Gly Tyr Ile
                165                 170                 175
```

-continued

```
att gga agt tgg gga aca ttg c                                          550
Ile Gly Ser Trp Gly Thr Leu
            180


<210> SEQ ID NO 18
<211> LENGTH: 183
<212> TYPE: PRT
<213> ORGANISM: Hepatitis B virus

<400> SEQUENCE: 18

Ser Ser Asn Leu Ser Trp Leu Ser Leu Asp Val Ser Ala Ala Phe Tyr
  1               5                  10                  15

His Ile Pro Leu His Pro Ala Ala Met Pro His Leu Leu Ile Gly Ser
             20                  25                  30

Ser Gly Leu Ser Arg Tyr Val Ala Arg Leu Ser Ser Asn Ser Arg Ile
         35                  40                  45

Asn Asn Asn Met Gln Asn Leu His Asp Ser Cys Ser Arg Gln Leu Tyr
     50                  55                  60

Val Ser Leu Met Leu Leu Tyr Lys Thr Tyr Gly Glu Lys Leu His Leu
 65                  70                  75                  80

Tyr Ser His Pro Ile Val Leu Gly Phe Arg Lys Ile Pro Met Gly Val
                 85                  90                  95

Gly Leu Ser Pro Phe Leu Leu Ala Gln Phe Thr Ser Ala Ile Cys Ser
            100                 105                 110

Val Val Arg Arg Ala Phe Pro His Cys Leu Ala Phe Ser Tyr Met Asp
        115                 120                 125

Asp Val Val Leu Gly Ala Lys Ser Val Gln His Arg Glu Ala Leu Tyr
    130                 135                 140

Thr Ala Val Thr Asn Phe Leu Leu Ser Leu Gly Ile His Leu Asn Pro
145                 150                 155                 160

Asn Lys Thr Lys Arg Trp Gly Tyr Ser Leu Asn Phe Met Gly Tyr Ile
                165                 170                 175

Ile Gly Ser Trp Gly Thr Leu
            180


<210> SEQ ID NO 19
<211> LENGTH: 550
<212> TYPE: DNA
<213> ORGANISM: Hepatitis B virus
<220> FEATURE:
<221> NAME/KEY: CDS
<222> LOCATION: (2)..(472)
<220> FEATURE:
<221> NAME/KEY: CDS
<222> LOCATION: (476)..(508)
<220> FEATURE:
<221> NAME/KEY: CDS
<222> LOCATION: (512)..(526)
<220> FEATURE:
<221> NAME/KEY: CDS
<222> LOCATION: (530)..(550)

<400> SEQUENCE: 19

t ctt cca att tgt cct ggt tat cgc tgg atg tgt ctg cgg cgt ttt atc      49
  Leu Pro Ile Cys Pro Gly Tyr Arg Trp Met Cys Leu Arg Arg Phe Ile
    1               5                  10                  15

ata ttc ctc ttc atc ctg ctg cta tgc ctc atc ttc tta ttg gtt ctt       97
Ile Phe Leu Phe Ile Leu Leu Leu Cys Leu Ile Phe Leu Leu Val Leu
             20                  25                  30

ctg gat tat caa ggt atg ttg ccc gtt tgt cct cta att cca gga tca      145
Leu Asp Tyr Gln Gly Met Leu Pro Val Cys Pro Leu Ile Pro Gly Ser
```

-continued

```
         35                  40                  45

aca aca aca tgc aaa acc tgc acg act cct gct caa ggc aac tct acg      193
Thr Thr Thr Cys Lys Thr Cys Thr Thr Pro Ala Gln Gly Asn Ser Thr
     50                  55                  60

ttt ccc tca tgt tgc tgt aca aaa cct acg gag aga aat tgc acc tgt      241
Phe Pro Ser Cys Cys Cys Thr Lys Pro Thr Glu Arg Asn Cys Thr Cys
 65                  70                  75                  80

att ccc atc cca tcg tcc tgg gct ttc gca aaa tac cta tgg gag tgg      289
Ile Pro Ile Pro Ser Ser Trp Ala Phe Ala Lys Tyr Leu Trp Glu Trp
                 85                  90                  95

gcc tca gtc cgt ttc tct tgg ctc agt tta cta gtg cca ttt gtt cag      337
Ala Ser Val Arg Phe Ser Trp Leu Ser Leu Leu Val Pro Phe Val Gln
            100                 105                 110

tgg ttc gta ggg ctt tcc ccc act gtt tgg ctt tca gct ata tgg atg      385
Trp Phe Val Gly Leu Ser Pro Thr Val Trp Leu Ser Ala Ile Trp Met
        115                 120                 125

atg tgg tat tgg ggg cca agt ctg tac agc atc gtg agg ccc ttt ata      433
Met Trp Tyr Trp Gly Pro Ser Leu Tyr Ser Ile Val Arg Pro Phe Ile
    130                 135                 140

ccg ctg tta cca att ttc ttt tgt ctc tgg gta tac att taa acc cta      481
Pro Leu Leu Pro Ile Phe Phe Cys Leu Trp Val Tyr Ile     Thr Leu
145                 150                 155

aca aaa caa aaa gat ggg gtt att ccc taa act tca tgg gtt aca taa      529
Thr Lys Gln Lys Asp Gly Val Ile Pro     Thr Ser Trp Val Thr
160                 165                     170

ttg gaa gtt ggg gaa cat tgc                                          550
Leu Glu Val Gly Glu His Cys
    175                 180


<210> SEQ ID NO 20
<211> LENGTH: 157
<212> TYPE: PRT
<213> ORGANISM: Hepatitis B virus

<400> SEQUENCE: 20

Leu Pro Ile Cys Pro Gly Tyr Arg Trp Met Cys Leu Arg Arg Phe Ile
  1               5                  10                  15

Ile Phe Leu Phe Ile Leu Leu Leu Cys Leu Ile Phe Leu Leu Val Leu
             20                  25                  30

Leu Asp Tyr Gln Gly Met Leu Pro Val Cys Pro Leu Ile Pro Gly Ser
         35                  40                  45

Thr Thr Thr Cys Lys Thr Cys Thr Thr Pro Ala Gln Gly Asn Ser Thr
     50                  55                  60

Phe Pro Ser Cys Cys Cys Thr Lys Pro Thr Glu Arg Asn Cys Thr Cys
 65                  70                  75                  80

Ile Pro Ile Pro Ser Ser Trp Ala Phe Ala Lys Tyr Leu Trp Glu Trp
                 85                  90                  95

Ala Ser Val Arg Phe Ser Trp Leu Ser Leu Leu Val Pro Phe Val Gln
            100                 105                 110

Trp Phe Val Gly Leu Ser Pro Thr Val Trp Leu Ser Ala Ile Trp Met
        115                 120                 125

Met Trp Tyr Trp Gly Pro Ser Leu Tyr Ser Ile Val Arg Pro Phe Ile
    130                 135                 140

Pro Leu Leu Pro Ile Phe Phe Cys Leu Trp Val Tyr Ile
145                 150                 155


<210> SEQ ID NO 21
<211> LENGTH: 11
```

-continued

<212> TYPE: PRT
<213> ORGANISM: Hepatitis B virus

<400> SEQUENCE: 21

Thr Leu Thr Lys Gln Lys Asp Gly Val Ile Pro
1 5 10

<210> SEQ ID NO 22
<211> LENGTH: 5
<212> TYPE: PRT
<213> ORGANISM: Hepatitis B virus

<400> SEQUENCE: 22

Thr Ser Trp Val Thr
1 5

<210> SEQ ID NO 23
<211> LENGTH: 7
<212> TYPE: PRT
<213> ORGANISM: Hepatitis B virus

<400> SEQUENCE: 23

Leu Glu Val Gly Glu His Cys
1 5

<210> SEQ ID NO 24
<211> LENGTH: 25
<212> TYPE: PRT
<213> ORGANISM: Hepatitis B virus
<220> FEATURE:
<221> NAME/KEY: VARIANT
<222> LOCATION: (1)
<223> OTHER INFORMATION: Xaa = Ser or Ala
<220> FEATURE:
<221> NAME/KEY: VARIANT
<222> LOCATION: (5)
<223> OTHER INFORMATION: Xaa = Ile or Val
<220> FEATURE:
<221> NAME/KEY: VARIANT
<222> LOCATION: (11)
<223> OTHER INFORMATION: Xaa = Ile or Leu
<220> FEATURE:
<221> NAME/KEY: VARIANT
<222> LOCATION: (15)
<223> OTHER INFORMATION: Xaa = Val or Gly

<400> SEQUENCE: 24

Xaa His Pro Ile Xaa Leu Gly Phe Arg Lys Xaa Pro Met Gly Xaa Gly
1 5 10 15

Leu Ser Pro Phe Leu Leu Ala Gln Phe
20 25

<210> SEQ ID NO 25
<211> LENGTH: 41
<212> TYPE: PRT
<213> ORGANISM: Hepatitis B virus
<220> FEATURE:
<221> NAME/KEY: VARIANT
<222> LOCATION: (1)
<223> OTHER INFORMATION: Xaa = Gln or Lys
<220> FEATURE:
<221> NAME/KEY: VARIANT
<222> LOCATION: (3)
<223> OTHER INFORMATION: Xaa = Tyr or Phe
<220> FEATURE:
<221> NAME/KEY: VARIANT
<222> LOCATION: (5)
<223> OTHER INFORMATION: Xaa = Arg or Trp
<220> FEATURE:
<221> NAME/KEY: VARIANT -continued <222> LOCATION: (10)
<223> OTHER INFORMATION: Xaa = Tyr or Leu
<220> FEATURE:
<221> NAME/KEY: VARIANT
<222> LOCATION: (11)
<223> OTHER INFORMATION: Xaa = Ser or Ala
<220> FEATURE:
<221> NAME/KEY: VARIANT
<222> LOCATION: (15)
<223> OTHER INFORMATION: Xaa = Ile or Val
<220> FEATURE:
<221> NAME/KEY: VARIANT
<222> LOCATION: (21)
<223> OTHER INFORMATION: Xaa = Ile or Leu
<220> FEATURE:
<221> NAME/KEY: VARIANT
<222> LOCATION: (25)
<223> OTHER INFORMATION: Xaa = Val or Gly
<220> FEATURE:
<221> NAME/KEY: VARIANT
<222> LOCATION: (40)
<223> OTHER INFORMATION: Xaa = Cys or Leu

<400> SEQUENCE: 25

```
Xaa Thr Xaa Gly Xaa Lys Leu His Leu Xaa Xaa His Pro Ile Xaa Leu
  1               5                  10                  15

Gly Phe Arg Lys Xaa Pro Met Gly Xaa Gly Leu Ser Pro Phe Leu Leu
             20                  25                  30

Ala Gln Phe Thr Ser Ala Ile Xaa Ser
         35                  40
```

<210> SEQ ID NO 26
<211> LENGTH: 11
<212> TYPE: PRT
<213> ORGANISM: Hepatitis B virus
<220> FEATURE:
<221> NAME/KEY: VARIANT
<222> LOCATION: (1)
<223> OTHER INFORMATION: Xaa = Ala or Val
<220> FEATURE:
<221> NAME/KEY: VARIANT
<222> LOCATION: (3)
<223> OTHER INFORMATION: Xaa = Ser or Ala
<220> FEATURE:
<221> NAME/KEY: VARIANT
<222> LOCATION: (8)
<223> OTHER INFORMATION: Xaa = Val or Leu or Met

<400> SEQUENCE: 26

```
Xaa Phe Xaa Tyr Met Asp Asp Xaa Val Leu Gly
  1               5                  10
```

<210> SEQ ID NO 27
<211> LENGTH: 30
<212> TYPE: PRT
<213> ORGANISM: Hepatitis B virus
<220> FEATURE:
<221> NAME/KEY: VARIANT
<222> LOCATION: (1)
<223> OTHER INFORMATION: Xaa = Ser or Ala
<220> FEATURE:
<221> NAME/KEY: VARIANT
<222> LOCATION: (5)
<223> OTHER INFORMATION: Xaa = Ile or Val
<220> FEATURE:
<221> NAME/KEY: VARIANT
<222> LOCATION: (8)
<223> OTHER INFORMATION: Xaa = Phe or Leu
<220> FEATURE:
<221> NAME/KEY: VARIANT
<222> LOCATION: (11)
<223> OTHER INFORMATION: Xaa = Ile or Leu
<220> FEATURE:

-continued

<221> NAME/KEY: VARIANT
<222> LOCATION: (15)
<223> OTHER INFORMATION: Xaa = Leu or Val or Gly
<220> FEATURE:
<221> NAME/KEY: VARIANT
<222> LOCATION: (19)
<223> OTHER INFORMATION: Xaa = Pro or Leu
<220> FEATURE:
<221> NAME/KEY: VARIANT
<222> LOCATION: (22)
<223> OTHER INFORMATION: Xaa = Leu or Met
<220> FEATURE:
<221> NAME/KEY: VARIANT
<222> LOCATION: (29)
<223> OTHER INFORMATION: Xaa = Ile or Leu
<220> FEATURE:
<221> NAME/KEY: VARIANT
<222> LOCATION: (30)
<223> OTHER INFORMATION: Xaa = Cys or Leu

<400> SEQUENCE: 27

Xaa His Pro Ile Xaa Leu Gly Xaa Arg Lys Xaa Pro Met Gly Xaa Gly
1 5 10 15

Leu Ser Xaa Phe Leu Xaa Ala Gln Phe Thr Ser Ala Xaa Xaa
20 25 30

<210> SEQ ID NO 28
<211> LENGTH: 14
<212> TYPE: PRT
<213> ORGANISM: Hepatitis B virus
<220> FEATURE:
<221> NAME/KEY: VARIANT
<222> LOCATION: (1)
<223> OTHER INFORMATION: Xaa = Ala or Val
<220> FEATURE:
<221> NAME/KEY: VARIANT
<222> LOCATION: (3)
<223> OTHER INFORMATION: Xaa = Ser or Ala
<220> FEATURE:
<221> NAME/KEY: VARIANT
<222> LOCATION: (5)
<223> OTHER INFORMATION: Xaa = Met or Ile or Val
<220> FEATURE:
<221> NAME/KEY: VARIANT
<222> LOCATION: (8)
<223> OTHER INFORMATION: Xaa = Val or Leu or Met
<220> FEATURE:
<221> NAME/KEY: VARIANT
<222> LOCATION: (13)
<223> OTHER INFORMATION: Xaa = Lys or Arg
<220> FEATURE:
<221> NAME/KEY: VARIANT
<222> LOCATION: (14)
<223> OTHER INFORMATION: Xaa = Ser or Thr

<400> SEQUENCE: 28

Xaa Phe Xaa Tyr Xaa Asp Asp Xaa Val Leu Gly Ala Xaa Xaa
1 5 10

<210> SEQ ID NO 29
<211> LENGTH: 181
<212> TYPE: PRT
<213> ORGANISM: Hepatitis B virus
<220> FEATURE:
<221> NAME/KEY: VARIANT
<222> LOCATION: (2)
<223> OTHER INFORMATION: Xaa = Asn or Asp
<220> FEATURE:
<221> NAME/KEY: VARIANT
<222> LOCATION: (17)
<223> OTHER INFORMATION: Xaa = Ile or Pro
<220> FEATURE:
<221> NAME/KEY: VARIANT
<222> LOCATION: (29)

-continued

<223> OTHER INFORMATION: Xaa = Ile or Val
<220> FEATURE:
<221> NAME/KEY: VARIANT
<222> LOCATION: (35)
<223> OTHER INFORMATION: Xaa = Ser or Asp
<220> FEATURE:
<221> NAME/KEY: VARIANT
<222> LOCATION: (44)
<223> OTHER INFORMATION: Xaa = Thr or Asn
<220> FEATURE:
<221> NAME/KEY: VARIANT
<222> LOCATION: (46)
<223> OTHER INFORMATION: Xaa = Arg or Asn
<220> FEATURE:
<221> NAME/KEY: VARIANT
<222> LOCATION: (47)
<223> OTHER INFORMATION: Xaa = Asn or Ile
<220> FEATURE:
<221> NAME/KEY: VARIANT
<222> LOCATION: (48)
<223> OTHER INFORMATION: Xaa = more than 3 different AA possible
<220> FEATURE:
<221> NAME/KEY: VARIANT
<222> LOCATION: (50)
<223> OTHER INFORMATION: Xaa = Asn orTyr or His
<220> FEATURE:
<221> NAME/KEY: VARIANT
<222> LOCATION: (52)
<223> OTHER INFORMATION: Xaa = His or Tyr
<220> FEATURE:
<221> NAME/KEY: VARIANT
<222> LOCATION: (53)
<223> OTHER INFORMATION: Xaa = Gly or Arg
<220> FEATURE:
<221> NAME/KEY: VARIANT
<222> LOCATION: (54)
<223> OTHER INFORMATION: Xaa = more than 3 different AA possible
<220> FEATURE:
<221> NAME/KEY: VARIANT
<222> LOCATION: (55)
<223> OTHER INFORMATION: Xaa = more than 3 different AA possible
<220> FEATURE:
<221> NAME/KEY: VARIANT
<222> LOCATION: (56)
<223> OTHER INFORMATION: Xaa = more than 3 different AA possible
<220> FEATURE:
<221> NAME/KEY: VARIANT
<222> LOCATION: (57)
<223> OTHER INFORMATION: Xaa = Asp or Asn
<220> FEATURE:
<221> NAME/KEY: VARIANT
<222> LOCATION: (60)
<223> OTHER INFORMATION: Xaa = Asp or Asn
<220> FEATURE:
<221> NAME/KEY: VARIANT
<222> LOCATION: (61)
<223> OTHER INFORMATION: Xaa = Ser or Tyr
<220> FEATURE:
<221> NAME/KEY: VARIANT
<222> LOCATION: (65)
<223> OTHER INFORMATION: Xaa = Asn or Gln
<220> FEATURE:
<221> NAME/KEY: VARIANT
<222> LOCATION: (71)
<223> OTHER INFORMATION: Xaa = Leu or Met
<220> FEATURE:
<221> NAME/KEY: VARIANT
<222> LOCATION: (75)
<223> OTHER INFORMATION: Xaa = Lys or Gln
<220> FEATURE:
<221> NAME/KEY: VARIANT
<222> LOCATION: (77)
<223> OTHER INFORMATION: Xaa = Tyr or Phe
<220> FEATURE:
<221> NAME/KEY: VARIANT
<222> LOCATION: (79)
<223> OTHER INFORMATION: Xaa = Arg or Trp
<220> FEATURE:
<221> NAME/KEY: VARIANT -continued <222> LOCATION: (84)
<223> OTHER INFORMATION: Xaa = Tyr or Leu
<220> FEATURE:
<221> NAME/KEY: VARIANT
<222> LOCATION: (85)
<223> OTHER INFORMATION: Xaa = Ser or Ala
<220> FEATURE:
<221> NAME/KEY: VARIANT
<222> LOCATION: (89)
<223> OTHER INFORMATION: Xaa = Ile or Val
<220> FEATURE:
<221> NAME/KEY: VARIANT
<222> LOCATION: (95)
<223> OTHER INFORMATION: Xaa = Ile or Leu
<220> FEATURE:
<221> NAME/KEY: VARIANT
<222> LOCATION: (99)
<223> OTHER INFORMATION: Xaa = Val or Gly
<220> FEATURE:
<221> NAME/KEY: VARIANT
<222> LOCATION: (114)
<223> OTHER INFORMATION: Xaa = Cys or Leu
<220> FEATURE:
<221> NAME/KEY: VARIANT
<222> LOCATION: (115)
<223> OTHER INFORMATION: Xaa = Ala or Ser
<220> FEATURE:
<221> NAME/KEY: VARIANT
<222> LOCATION: (116)
<223> OTHER INFORMATION: Xaa = Val or Met
<220> FEATURE:
<221> NAME/KEY: VARIANT
<222> LOCATION: (117)
<223> OTHER INFORMATION: Xaa = Val or Thr
<220> FEATURE:
<221> NAME/KEY: VARIANT
<222> LOCATION: (118)
<223> OTHER INFORMATION: Xaa = Arg or Cys
<220> FEATURE:
<221> NAME/KEY: VARIANT
<222> LOCATION: (122)
<223> OTHER INFORMATION: Xaa = Phe or Pro
<220> FEATURE:
<221> NAME/KEY: VARIANT
<222> LOCATION: (125)
<223> OTHER INFORMATION: Xaa = Leu or Val
<220> FEATURE:
<221> NAME/KEY: VARIANT
<222> LOCATION: (126)
<223> OTHER INFORMATION: Xaa = Ala or Val
<220> FEATURE:
<221> NAME/KEY: VARIANT
<222> LOCATION: (128)
<223> OTHER INFORMATION: Xaa = Ser or Ala
<220> FEATURE:
<221> NAME/KEY: VARIANT
<222> LOCATION: (133)
<223> OTHER INFORMATION: Xaa = Val or Leu or Met
<220> FEATURE:
<221> NAME/KEY: VARIANT
<222> LOCATION: (138)
<223> OTHER INFORMATION: Xaa = Lys or Arg
<220> FEATURE:
<221> NAME/KEY: VARIANT
<222> LOCATION: (139)
<223> OTHER INFORMATION: Xaa = Ser or Thr
<220> FEATURE:
<221> NAME/KEY: VARIANT
<222> LOCATION: (140)
<223> OTHER INFORMATION: Xaa = Val or Gly
<220> FEATURE:
<221> NAME/KEY: VARIANT
<222> LOCATION: (141)
<223> OTHER INFORMATION: Xaa = Gln or Glu
<220> FEATURE:
<221> NAME/KEY: VARIANT
<222> LOCATION: (143)
<223> OTHER INFORMATION: Xaa = Leu or Ser or Arg
<220> FEATURE:

-continued

<221> NAME/KEY: VARIANT
<222> LOCATION: (145)
<223> OTHER INFORMATION: Xaa = Ser or Phe
<220> FEATURE:
<221> NAME/KEY: VARIANT
<222> LOCATION: (147)
<223> OTHER INFORMATION: Xaa = Phe or Tyr
<220> FEATURE:
<221> NAME/KEY: VARIANT
<222> LOCATION: (148)
<223> OTHER INFORMATION: Xaa = Thr or Ala
<220> FEATURE:
<221> NAME/KEY: VARIANT
<222> LOCATION: (149)
<223> OTHER INFORMATION: Xaa = Ala or Ser
<220> FEATURE:
<221> NAME/KEY: VARIANT
<222> LOCATION: (150)
<223> OTHER INFORMATION: Xaa = Val or Ile
<220> FEATURE:
<221> NAME/KEY: VARIANT
<222> LOCATION: (151)
<223> OTHER INFORMATION: Xaa = Thr or Cys
<220> FEATURE:
<221> NAME/KEY: VARIANT
<222> LOCATION: (152)
<223> OTHER INFORMATION: Xaa = Asn or Ser
<220> FEATURE:
<221> NAME/KEY: VARIANT
<222> LOCATION: (153)
<223> OTHER INFORMATION: Xaa = Phe or Val
<220> FEATURE:
<221> NAME/KEY: VARIANT
<222> LOCATION: (156)
<223> OTHER INFORMATION: Xaa = Ser or Asp
<220> FEATURE:
<221> NAME/KEY: VARIANT
<222> LOCATION: (157)
<223> OTHER INFORMATION: Xaa = Leu or Val
<220> FEATURE:
<221> NAME/KEY: VARIANT
<222> LOCATION: (164)
<223> OTHER INFORMATION: Xaa = Asn or Gln
<220> FEATURE:
<221> NAME/KEY: VARIANT
<222> LOCATION: (179)
<223> OTHER INFORMATION: Xaa = Val or Ile

<400> SEQUENCE: 29

```
Ser Xaa Leu Ser Trp Leu Ser Leu Asp Val Ser Ala Ala Phe Tyr His
  1               5                  10                  15

Xaa Pro Leu His Pro Ala Ala Met Pro His Leu Leu Xaa Gly Ser Ser
             20                  25                  30

Gly Leu Xaa Arg Tyr Val Ala Arg Leu Ser Ser Xaa Ser Xaa Xaa Xaa
         35                  40                  45

Asn Xaa Gln Xaa Xaa Xaa Xaa Xaa Xaa Leu His Xaa Xaa Cys Ser Arg
     50                  55                  60

Xaa Leu Tyr Val Ser Leu Xaa Leu Leu Tyr Xaa Thr Xaa Gly Xaa Lys
 65                  70                  75                  80

Leu His Leu Xaa Xaa His Pro Ile Xaa Leu Gly Phe Arg Lys Xaa Pro
                 85                  90                  95

Met Gly Xaa Gly Leu Ser Pro Phe Leu Leu Ala Gln Phe Thr Ser Ala
            100                 105                 110

Ile Xaa Xaa Xaa Xaa Xaa Arg Ala Phe Xaa His Cys Xaa Xaa Phe Xaa
        115                 120                 125

Tyr Met Asp Asp Xaa Val Leu Gly Ala Xaa Xaa Xaa Xaa His Xaa Glu
    130                 135                 140

Xaa Leu Xaa Xaa Xaa Xaa Xaa Xaa Xaa Leu Leu Xaa Xaa Gly Ile His
145                 150                 155                 160
```

```
Leu Asn Pro Xaa Lys Thr Lys Arg Trp Gly Tyr Ser Leu Asn Phe Met
                165                 170                 175

Gly Tyr Xaa Ile Gly
            180


<210> SEQ ID NO 30
<211> LENGTH: 4
<212> TYPE: PRT
<213> ORGANISM: Hepatitis B virus

<400> SEQUENCE: 30

Tyr Met Asp Asp
  1


<210> SEQ ID NO 31
<211> LENGTH: 11
<212> TYPE: PRT
<213> ORGANISM: Hepatitis B virus

<400> SEQUENCE: 31

Ala Phe Ser Tyr Met Asp Asp Val Val Leu Gly
  1               5                  10


<210> SEQ ID NO 32
<211> LENGTH: 11
<212> TYPE: PRT
<213> ORGANISM: Hepatitis B virus

<400> SEQUENCE: 32

Ala Phe Ser Tyr Met Asp Asp Val Val Leu Gly
  1               5                  10


<210> SEQ ID NO 33
<211> LENGTH: 11
<212> TYPE: PRT
<213> ORGANISM: Hepatitis B virus

<400> SEQUENCE: 33

Val Phe Ala Tyr Met Asp Asp Leu Val Leu Gly
  1               5                  10


<210> SEQ ID NO 34
<211> LENGTH: 11
<212> TYPE: PRT
<213> ORGANISM: Hepatitis B virus

<400> SEQUENCE: 34

Ile Tyr Gln Tyr Met Asp Asp Leu Tyr Val Gly
  1               5                  10


<210> SEQ ID NO 35
<211> LENGTH: 33
<212> TYPE: PRT
<213> ORGANISM: Hepatitis B virus

<400> SEQUENCE: 35

Thr Thr Ile Gly Arg Glu Met Leu Leu Ala Thr Arg Glu Tyr Val His
  1               5                  10                  15

Ala Arg Trp Ala Ala Phe Glu Gln Leu Leu Ala Asp Phe Pro Glu Ala
             20                  25                  30

Ala
```

-continued

<210> SEQ ID NO 36
<211> LENGTH: 41
<212> TYPE: PRT
<213> ORGANISM: Hepatitis B virus

<400> SEQUENCE: 36

Gln Thr Phe Gly Arg Lys Leu His Leu Tyr Ser His Pro Ile Ile Leu
1 5 10 15

Gly Phe Arg Lys Ile Pro Met Gly Leu Gly Leu Ser Leu Phe Leu Met
20 25 30

Ala Gln Phe Thr Ser Ala Ile Cys Ser
35 40

<210> SEQ ID NO 37
<211> LENGTH: 41
<212> TYPE: PRT
<213> ORGANISM: Hepatitis B virus

<400> SEQUENCE: 37

Gln Thr Phe Gly Arg Lys Leu His Leu Tyr Ser His Pro Ile Ile Leu
1 5 10 15

Gly Phe Arg Lys Ile Pro Met Gly Val Gly Leu Ser Pro Phe Leu Met
20 25 30

Ala Gln Phe Thr Ser Ala Ile Cys Ser
35 40

<210> SEQ ID NO 38
<211> LENGTH: 41
<212> TYPE: PRT
<213> ORGANISM: Hepatitis B virus

<400> SEQUENCE: 38

Gln Thr Phe Gly Arg Lys Leu His Leu Tyr Ser His Pro Ile Ile Leu
1 5 10 15

Gly Leu Arg Lys Ile Pro Met Gly Val Gly Leu Ser Pro Phe Leu Met
20 25 30

Ala Gln Phe Thr Ser Ala Ile Cys Ser
35 40

<210> SEQ ID NO 39
<211> LENGTH: 41
<212> TYPE: PRT
<213> ORGANISM: Hepatitis B virus

<400> SEQUENCE: 39

Gln Thr Phe Gly Arg Lys Leu His Leu Tyr Ser His Pro Ile Val Leu
1 5 10 15

Gly Phe Arg Lys Ile Pro Met Gly Val Gly Leu Ser Pro Phe Leu Leu
20 25 30

Ala Gln Phe Thr Ser Ala Leu Cys Ser
35 40

<210> SEQ ID NO 40
<211> LENGTH: 14
<212> TYPE: PRT
<213> ORGANISM: Hepatitis B virus

<400> SEQUENCE: 40

Ala Phe Ser Tyr Met Asp Asp Val Val Leu Gly Ala Lys Thr
1 5 10

-continued

<210> SEQ ID NO 41
<211> LENGTH: 31
<212> TYPE: PRT
<213> ORGANISM: Hepatitis B virus
<220> FEATURE:
<221> NAME/KEY: VARIANT
<222> LOCATION: (1)
<223> OTHER INFORMATION: Xaa = Ser or Ala
<220> FEATURE:
<221> NAME/KEY: VARIANT
<222> LOCATION: (5)
<223> OTHER INFORMATION: Xaa = Ile or Val
<220> FEATURE:
<221> NAME/KEY: VARIANT
<222> LOCATION: (11)
<223> OTHER INFORMATION: Xaa = Ile or Leu
<220> FEATURE:
<221> NAME/KEY: VARIANT
<222> LOCATION: (15)
<223> OTHER INFORMATION: Xaa = Val or Gly

<400> SEQUENCE: 41

```
Xaa His Pro Ile Xaa Leu Gly Phe Arg Lys Xaa Pro Met Gly Xaa Gly
  1               5                  10                  15

Leu Ser Pro Phe Leu Leu Ala Gln Phe Thr Ser Ala Ile Cys Ser
             20                  25                  30
```

<210> SEQ ID NO 42
<211> LENGTH: 40
<212> TYPE: PRT
<213> ORGANISM: Hepatitis B virus
<220> FEATURE:
<221> NAME/KEY: VARIANT
<222> LOCATION: (1)
<223> OTHER INFORMATION: Xaa = Gln or Lys
<220> FEATURE:
<221> NAME/KEY: VARIANT
<222> LOCATION: (3)
<223> OTHER INFORMATION: Xaa = Tyr or Phe
<220> FEATURE:
<221> NAME/KEY: VARIANT
<222> LOCATION: (5)
<223> OTHER INFORMATION: Xaa = Arg or Trp  or Glu
<220> FEATURE:
<221> NAME/KEY: VARIANT
<222> LOCATION: (10)
<223> OTHER INFORMATION: Xaa = Tyr or Leu
<220> FEATURE:
<221> NAME/KEY: VARIANT
<222> LOCATION: (11)
<223> OTHER INFORMATION: Xaa = Ser or Ala
<220> FEATURE:
<221> NAME/KEY: VARIANT
<222> LOCATION: (15)
<223> OTHER INFORMATION: Xaa = Ile or Val
<220> FEATURE:
<221> NAME/KEY: VARIANT
<222> LOCATION: (18)
<223> OTHER INFORMATION: Xaa = Phe or Leu
<220> FEATURE:
<221> NAME/KEY: VARIANT
<222> LOCATION: (21)
<223> OTHER INFORMATION: Xaa = Ile or Leu
<220> FEATURE:
<221> NAME/KEY: VARIANT
<222> LOCATION: (25)
<223> OTHER INFORMATION: Xaa = Leu or Val or Glu
<220> FEATURE:
<221> NAME/KEY: VARIANT
<222> LOCATION: (29)
<223> OTHER INFORMATION: Xaa = Pro or Leu
<220> FEATURE:
<221> NAME/KEY: VARIANT
<222> LOCATION: (32)
<223> OTHER INFORMATION: Xaa = Leu or Met
<220> FEATURE:

-continued

<221> NAME/KEY: VARIANT
<222> LOCATION: (39)
<223> OTHER INFORMATION: Xaa = Ile or Leu
<220> FEATURE:
<221> NAME/KEY: VARIANT
<222> LOCATION: (40)
<223> OTHER INFORMATION: Xaa = Cys or Leu

<400> SEQUENCE: 42

Xaa Thr Xaa Gly Xaa Lys Leu His Leu Xaa Xaa His Pro Ile Xaa Leu
1 5 10 15

Gly Xaa Arg Lys Xaa Pro Met Gly Xaa Gly Leu Ser Xaa Phe Leu Xaa
20 25 30

Ala Gln Phe Thr Ser Ala Xaa Xaa
35 40

<210> SEQ ID NO 43
<211> LENGTH: 14
<212> TYPE: PRT
<213> ORGANISM: Hepatitis B virus
<220> FEATURE:
<221> NAME/KEY: VARIANT
<222> LOCATION: (1)
<223> OTHER INFORMATION: Xaa = Ala or Val
<220> FEATURE:
<221> NAME/KEY: VARIANT
<222> LOCATION: (3)
<223> OTHER INFORMATION: Xaa = Ser or Ala
<220> FEATURE:
<221> NAME/KEY: VARIANT
<222> LOCATION: (5)
<223> OTHER INFORMATION: Xaa = Met or Ile or Val
<220> FEATURE:
<221> NAME/KEY: VARIANT
<222> LOCATION: (8)
<223> OTHER INFORMATION: Xaa = Val or Leu or Met
<220> FEATURE:
<221> NAME/KEY: VARIANT
<222> LOCATION: (13)
<223> OTHER INFORMATION: Xaa = Lys or Arg
<220> FEATURE:
<221> NAME/KEY: VARIANT
<222> LOCATION: (14)
<223> OTHER INFORMATION: Xaa = Ser or Thr

<400> SEQUENCE: 43

Xaa Phe Xaa Tyr Xaa Asp Asp Xaa Val Leu Gly Ala Xaa Xaa
1 5 10

<210> SEQ ID NO 44
<211> LENGTH: 31
<212> TYPE: PRT
<213> ORGANISM: Hepatitis B virus
<220> FEATURE:
<221> NAME/KEY: VARIANT
<222> LOCATION: (1)
<223> OTHER INFORMATION: Xaa = Ser or Ala
<220> FEATURE:
<221> NAME/KEY: VARIANT
<222> LOCATION: (5)
<223> OTHER INFORMATION: Xaa = Ile or Val
<220> FEATURE:
<221> NAME/KEY: VARIANT
<222> LOCATION: (11)
<223> OTHER INFORMATION: Xaa = Ile or Leu
<220> FEATURE:
<221> NAME/KEY: VARIANT
<222> LOCATION: (15)
<223> OTHER INFORMATION: Xaa = Val or Gly
<220> FEATURE:
<221> NAME/KEY: VARIANT
<222> LOCATION: (30)
<223> OTHER INFORMATION: Xaa = Cys or Leu

<400> SEQUENCE: 44

Xaa His Pro Ile Xaa Leu Gly Phe Arg Lys Xaa Pro Met Gly Xaa Gly
1 5 10 15

Leu Ser Pro Phe Leu Leu Ala Gln Phe Thr Ser Ala Ile Xaa Ser
20 25 30

<210> SEQ ID NO 45
<211> LENGTH: 14
<212> TYPE: PRT
<213> ORGANISM: Hepatitis B virus
<220> FEATURE:
<221> NAME/KEY: VARIANT
<222> LOCATION: (1)
<223> OTHER INFORMATION: Xaa = Ala or Val
<220> FEATURE:
<221> NAME/KEY: VARIANT
<222> LOCATION: (3)
<223> OTHER INFORMATION: Xaa = Ser or Ala
<220> FEATURE:
<221> NAME/KEY: VARIANT
<222> LOCATION: (8)
<223> OTHER INFORMATION: Xaa = Val or Leu or Met
<220> FEATURE:
<221> NAME/KEY: VARIANT
<222> LOCATION: (13)
<223> OTHER INFORMATION: Xaa = Lys or Arg
<220> FEATURE:
<221> NAME/KEY: VARIANT
<222> LOCATION: (14)
<223> OTHER INFORMATION: Xaa = Ser or Thr

<400> SEQUENCE: 45

Xaa Phe Xaa Tyr Met Asp Asp Xaa Val Leu Gly Ala Xaa Xaa
1 5 10

<210> SEQ ID NO 46
<211> LENGTH: 11
<212> TYPE: PRT
<213> ORGANISM: Hepatitis B virus

<400> SEQUENCE: 46

Ala Phe Ser Tyr Met Asp Asp Val Val Leu Gly
1 5 10

<210> SEQ ID NO 47
<211> LENGTH: 11
<212> TYPE: PRT
<213> ORGANISM: Hepatitis B virus

<400> SEQUENCE: 47

Ala Phe Ser Tyr Met Asp Asp Val Val Leu Gly
1 5 10

<210> SEQ ID NO 48
<211> LENGTH: 11
<212> TYPE: PRT
<213> ORGANISM: Hepatitis B virus
<220> FEATURE:
<221> NAME/KEY: VARIANT
<222> LOCATION: (5)
<223> OTHER INFORMATION: Xaa = Val or Ile

<400> SEQUENCE: 48

Ala Phe Ser Tyr Xaa Asp Asp Val Val Leu Gly
1 5 10

<210> SEQ ID NO 49

<211> LENGTH: 11
<212> TYPE: PRT
<213> ORGANISM: Hepatitis B virus

<400> SEQUENCE: 49

Ala Phe Ser Tyr Met Asp Asp Val Val Leu Gly
1 5 10

<210> SEQ ID NO 50
<211> LENGTH: 16
<212> TYPE: PRT
<213> ORGANISM: Hepatitis B virus

<400> SEQUENCE: 50

Ser Asp Leu Ser Trp Leu Ser Leu Asp Val Ser Ala Ala Phe Tyr His
1 5 10 15

<210> SEQ ID NO 51
<211> LENGTH: 16
<212> TYPE: PRT
<213> ORGANISM: Hepatitis B virus

<400> SEQUENCE: 51

Ser Asp Leu Ser Trp Leu Ser Leu Asp Val Ser Ala Ala Phe Tyr His
1 5 10 15

<210> SEQ ID NO 52
<211> LENGTH: 16
<212> TYPE: PRT
<213> ORGANISM: Hepatitis B virus

<400> SEQUENCE: 52

Thr Asp Leu Gln Trp Leu Ser Leu Asp Val Ser Ala Ala Phe Tyr His
1 5 10 15

<210> SEQ ID NO 53
<211> LENGTH: 16
<212> TYPE: PRT
<213> ORGANISM: Hepatitis B virus

<400> SEQUENCE: 53

Lys Lys Lys Ser Val Thr Val Leu Asp Val Gly Asp Ala Tyr Phe Ser
1 5 10 15

<210> SEQ ID NO 54
<211> LENGTH: 41
<212> TYPE: PRT
<213> ORGANISM: Hepatitis B virus

<400> SEQUENCE: 54

Gln Thr Phe Gly Arg Lys Leu His Leu Tyr Ser His Pro Ile Ile Leu
1 5 10 15

Gly Phe Arg Lys Ile Pro Met Gly Val Gly Leu Ser Pro Phe Leu Leu
20 25 30

Ala Gln Phe Thr Ser Ala Ile Cys Ser
35 40

<210> SEQ ID NO 55
<211> LENGTH: 41
<212> TYPE: PRT
<213> ORGANISM: Hepatitis B virus

<400> SEQUENCE: 55

Gln Thr Phe Gly Arg Lys Leu His Leu Tyr Ser His Pro Ile Ile Leu

-continued

```
  1               5                   10                  15

Gly Phe Arg Lys Ile Pro Met Gly Leu Gly Leu Ser Leu Phe Leu Met
            20                  25                  30

Ala Gln Phe Thr Ser Ala Ile Cys Ser
        35                  40


<210> SEQ ID NO 56
<211> LENGTH: 41
<212> TYPE: PRT
<213> ORGANISM: Hepatitis B virus

<400> SEQUENCE: 56

Lys Thr Tyr Gly Arg Lys Leu His Leu Leu Ala His Pro Phe Ile Met
  1               5                   10                  15

Gly Phe Arg Lys Leu Phe Met Gly Val Gly Leu Ser Pro Phe Leu Leu
            20                  25                  30

Ala Gln Phe Thr Ser Ala Leu Ala Ser
        35                  40


<210> SEQ ID NO 57
<211> LENGTH: 27
<212> TYPE: PRT
<213> ORGANISM: Hepatitis B virus

<400> SEQUENCE: 57

Arg Tyr Gln Tyr Asn Val Leu Pro Gln Gly Trp Lys Gly Ser Pro Ala
  1               5                   10                  15

Ile Phe Gln Ser Ser Met Thr Lys Ile Leu Glu
            20                  25
```

What is claimed is:

1. An isolated HBV mutant, comprising a mutation in the gene encoding the HBV DNA polymerase resulting in decreased sensitivity to a nucleoside analogue compared to a wild-type HBV, wherein said mutation results in at least one amino acid addition, substitution, and/or deletion in the B domain corresponding to amino acid residues 495–535 of a wild-type HBV polymerase, and said mutant contains an unmutated YMDD motif in the C domain.

2. An isolated HBV mutant, comprising a mutation in the gene encoding the HBV DNA polymerase resulting in decreased sensitivity to a nucleoside analogue compared to a wild-type HBV, wherein said mutation results in at least one amino acid addition, substitution, and/or deletion in the B domain corresponding to amino acid residues 505–535 of a wild-type HBV polymerase, and said mutant contains an unmutated YMDD motif in the C domain.

3. An isolated HBV mutant, comprising a mutation in the gene encoding the HBV DNA polymerase resulting in decreased sensitivity to a nucleoside analogue compared to a wild-type HBV, wherein said mutation results in at least one amino acid addition, substitution, and/or deletion in the B domain corresponding to amino acid residues 505–529 of a wild-type HBV polymerase, and said mutant contains an unmutated YMDD motif in the C domain.

4. An isolated HBV mutant exhibiting, relative to an isolated wild-type HBV, reduced sensitivity to a nucleoside analogue and reduced interactivity to an antibody to a wild-type HBV surface antigen, said HBV mutant comprising at least one of:

(i) a nucleotide sequence of its genome as set forth in SEQ ID NO:17 or a sequence having at least 60% similarity thereto;

(ii) a nucleotide sequence capable of hybridising to SEQ ID NO:17 under low stringency conditions at 42° C.;

(iii) a mutation in an overlapping portion of open reading frames for DNA polymerase and HBV surface antigen; and (iv) a mutation in a region corresponding to amino acids 118 to 169 and/or 169 to 207 of HBV surface antigen, wherein said mutant contains a Trp/Arg499Glu amino acid substitution in the DNA polymerase and an Asp144Glu and Gly145Arg amino acid substitution in the surface antigen.

5. The isolated HBV mutant according to any of claim 1 or 4 wherein said nucleoside analogue is selected from the group consisting of famciclovir, penciclovir and lamivudine.

6. The HBV mutant according to any of claim 1 or 4 wherein said mutation is selected from the group consisting of Arg/Trp499Glu, Phe512Leu, Val519Leu, Pro523Leu, Leu526Met, Thr530Ser, and Ile533Leu.

7. The HBV mutant according to claim 5 wherein said mutation is selected from the group consisting of Arg/Trp499Glu, Phe512Leu, Val519Leu, Pro523Leu, Leu526Met, Thr530Ser, and Ile533Leu.

8. An isolated HBV mutant exhibiting, relative to an isolated wild-type HBV, reduced sensitivity to a nucleoside analogue, said mutant comprising at least one mutation in its genome wherein said at least one mutation produces at least one amino acid substitution in the DNA polymerase selected from the group consisting of Trp/Arg499Glu, Phe512Leu and Val519Leu, said amino acid substitution in the DNA polymerase resulting in a concurrent amino acid substitution in the overlapping open reading frame of the HBV surface antigen, and said mutant contains an unmutated YMDD motif in the C domain.

9. An isolated HBV mutant exhibiting, relative to an isolated wild-type HBV, reduced sensitivity to a nucleoside analogue, said mutant comprising at least one mutation in its genome wherein said at least one mutation produces at least one amino acid substitution in the DNA polymerase selected from the group consisting of Trp/Arg499Glu, Phe512Leu, Val519Leu and Ser559Thr, said amino acid substitution in the DNA polymerase resulting in a concurrent amino acid substitution in the overlapping open reading frame of the HBV surface antigen, and said mutant contains an unmutated YMDD motif in the C domain.

10. An isolated mutant according to claim 8 or 9 wherein said nucleoside analogue is selected from the group consisting of famciclovir, penciclovir and lamivudine.

11. A method for determining the potential for an HBV to exhibit, relative to an isolated wild-type HBV, reduced sensitivity to at least one of lamivudine, penciclovir and famciclovir, said method comprising isolating DNA or corresponding mRNA from said HBV and screening for a mutation in a nucleotide sequence encoding the B domain of HBV polymerase, corresponding to amino acid residues 495–535 of a wild-type HBV polymerase, with said mutation resulting in at least one amino acid substitution, deletion and/or addition in said B domain, wherein the presence of such a mutation is an indication of the potential of reduced sensitivity of said HBV to at least one of lamivudine, penciclovir and famciclovir.

12. A method for determining the potential for an HBV to exhibit, relative to an isolated wild-type HBV, reduced sensitivity to at least one of lamivudine, penciclovir and famciclovir, said method comprising isolating DNA or corresponding mRNA from said HBV and screening for a mutation in a nucleotide sequence encoding the B domain of HBV polymerase corresponding to amino acid residues 505–535 of a wild-type HBV polymerase, with said mutation resulting in at least one amino acid substitution, deletion and/or addition in said B domain, wherein the presence of such a mutation is an indication of the potential of reduced sensitivity of said HBV to at least one of lamivudine, penciclovir and famciclovir.

13. A method for determining the potential for an HBV to exhibit, relative to an isolated wild-type HBV, reduced sensitivity to at least one of lamivudine, penciclovir and famciclovir, said method comprising isolating DNA or corresponding mRNA from said HBV and screening for a mutation in a nucleotide sequence encoding the B domain of HBV polymerase corresponding to amino acid residues 505–529 of a wild-type HBV polymerase, with said mutation resulting in at least one amino acid substitution, deletion and/or addition in said B domain, wherein the presence of such a mutation is an indication of the potential of reduced sensitivity of said HBV to at least one of lamivudine, penciclovir and famciclovir.

14. A method for determining the potential for an HBV to exhibit, relative to an isolated wild-type HBV, reduced sensitivity to at least one of lamivudine, penciclovir and famciclovir, said method comprising isolating DNA or corresponding mRNA from said HBV and screening for a mutation in a nucleotide sequence encoding HBV DNA polymerase, wherein the screening detects at least one mutation selected from the group consisting of Arg/Trp499Glu, Phe512Leu, Val 519Leu, Pro523Leu, Leu526Met, Thr530Ser, Ile533Leu, Met550Val and Met550Ile, such that when said at least one amino substitution in the DNA polymerase is Met550Val or Met550Ile, said method detects at least one amino acid substitution other than Phe512Leu, Leu526Met or Val553Ile, wherein the presence of such a mutation is an indication of the potential of reduced sensitivity of said HBV to at least one of lamivudine, penciclovir and famciclovir.

15. A method for determining the potential for an HBV to exhibit, relative to an isolated wild-type HBV, reduced sensitivity to at least one of penciclovir and famciclovir, said method comprising isolating DNA or corresponding mRNA from said HBV and screening for a mutation in a nucleotide sequence encoding HBV DNA polymerase, wherein the screening detects at least one mutation selected from the group consisting of Arg/Trp499Glu, Phe512Leu, Val 519Leu, Pro523Leu, Leu526Met, Thr530Ser, Ile533Leu, Met550Val and Met550Ile, wherein the presence of such a mutation is an indication of the potential of reduced sensitivity of said HBV to at least one of penciclovir and famciclovir.

16. The method according to any of claim 11, 14 or 15, wherein the screening for a mutation comprises sequencing said isolated HBV DNA or corresponding mRNA.

17. The method according to any of claim 11, 14 or 15, wherein the screening for a mutation comprises a PCR method or PCR-based method.

18. The method according to any of claim 11, 14 or 15, wherein the screening for a mutation comprises a hybridization method.

19. An isolated Hepadnavirus mutant, comprising a mutation in the gene encoding the DNA polymerase, resulting in decreased sensitivity to a nucleoside analogue compared to a wild-type Hepadnavirus, wherein said mutation results in at least one amino acid addition, substitution, and/or deletion in the B domain corresponding to amino acid residues 495–535 of a wild-type HBV polymerase, and said mutant contains an unmutated YMDD motif in the C domain.

20. An isolated Hepadnavirus mutant, comprising a mutation in the gene encoding the DNA polymerase, resulting in decreased sensitivity to a nucleoside analogue compared to a wild-type Hepadnavirus, wherein said mutation results in at least one amino acid addition, substitution, and/or deletion in the B domain corresponding to amino acid residues 505–535 of a wild-type HBV polymerase, and said mutant contains an unmutated YMDD motif in the C domain.

21. An isolated Hepadnavirus mutant, comprising a mutation in the gene encoding the DNA polymerase, resulting in decreased sensitivity to a nucleoside analogue compared to a wild-type Hepadnavirus, wherein said mutation results in at least one amino acid addition, substitution, and/or deletion in the B domain corresponding to amino acid residues 505–529 of a wild-type HBV polymerase, and said mutant contains an unmutated YMDD motif in the C domain.

22. An isolated mutant according to claim 19, wherein the nucleoside analogue is selected from the groups consisting of famciclovir, penciclovir and lamivudine.

23. An isolated mutant according to claim 19 or 22, wherein the Hepadhavirus is woodchuck hepatitis virus.

24. An isolated mutant according to claim 19 or 22, wherein the Hepadnavirus is duck hepatitis virus.

25. A method for determining the potential for an HBV to exhibit, relative to an isolated wild-type HBV, reduced sensitivity to an anti-viral agent, said method comprising isolating DNA or corresponding mRNA from said HBV and screening for a mutation in a nucleotide sequence encoding the B domain of HBV polymerase corresponding to amino acid residues 495–535 of a wild-type HBV polymerase, with said mutation resulting in at least one amino acid substitution, deletion and/or addition in said B domain, wherein the presence of such a mutation is an indication of the potential of reduced sensitivity of said HBV to an anti-viral agent.

*26. An isolated HBV mutant with a single mutation affecting the normal function of the DNA polymerase resulting in decreased sensitivity to a nucleoside analogue compared to a wild-type HBV, wherein the mutation consists of an amino acid addition, substitution or deletion in the B*

*domain corresponding to amino acid residues 495–535 of a wild-type HBV polymerase.*

*27. An isolated HBV mutant with a single mutation affecting the normal function of the DNA polymerase resulting in decreased sensitivity to a nucleoside analogue compared to a wild-type HBV, wherein the mutation consists of an amino acid addition, substitution or deletion in the B domain corresponding to amino acid residues 505–535 of a wild-type HBV polymerase.*

*28. An isolated HBV mutant with a single mutation affecting the normal function of the DNA polymerase resulting in decreased sensitivity to a nucleoside analogue compared to a wild-type HBV, wherein the mutation consists of an amino acid addition, substitution or deletion in the B domain corresponding to amino acid residues 505–529 of a wild-type HBV polymerase.*

*29. An isolated HBV mutant with a single mutation affecting the normal function of the DNA polymerase resulting in decreased sensitivity to a nucleoside analogue compared to a wild-type HBV and affecting the interactivity of an antibody to a wild-type HBV surface antigen, wherein said HBV mutant comprises at least one of*

*(i) a nucleotide sequence of its genome as set forth in SEQ ID NO:17 or a sequence having at least 60% similarity thereto;*

*(ii) a nucleotide sequence capable of hybridising to SEQ ID NO:17 under low stringency conditions at 42° C.;*

*(iii) a mutation in an overlapping portion of open reading frames for DNA polymerase and HBV surface antigen; and*

*(iv) a mutation in a region corresponding to amino acids 118 to 169 and/or 169 to 207 of HBV surface antigen,*

*wherein said mutant contains a Trp/Arg499Glu amino acid substitution in the DNA polymerase and an Asp144Glu and Gly145Arg amino acid substitution in the surface antigen.*

*30. The isolated HBV mutant according to claim 26 wherein said nucleoside analogue is selected from the group consisting of famciclovir, penciclovir and lamivudine.*

*31. The HBV mutant according to claim 26 wherein said mutation is selected from the group consisting of Arg/Trp499Glu, Phe512Leu, Val519Leu, Pro523Leu, Leu526Met, Thr530Ser, and Ile533Leu.*

*32. An isolated HBV mutant with a single mutation affecting the normal function of the DNA polymerase resulting in decreased sensitivity to a nucleoside analogue selected from the group consisting of famciclovir, penciclovir and lamivudine, compared to a wild-type HBV, wherein the mutation is selected from the group consisting of Arg/Trp499Glu, Phe512Leu, Val519Leu, Pro523Leu, Leu526Met, Thr530Ser, and Ile533Leu.*

*33. An isolated Hepadnavirus mutant with a single mutation affecting the normal function of the DNA polymerase resulting in decreased sensitivity to a nucleoside analogue compared to a wild-type Hepadnavirus, wherein said mutation consists of an amino acid addition, substitution or deletion in the B domain corresponding to amino acid residues 495–535 of a wild-type HBV polymerase.*

*34. An isolated Hepadnavirus mutant with a single mutation affecting the normal function of the DNA polymerase resulting in decreased sensitivity to a nucleoside analogue compared to a wild-type Hepadnavirus, wherein said mutation consists of an amino acid addition, substitution or deletion in the B domain corresponding to amino acid residues 505–535 of a wild-type HBV polymerase.*

*35. An isolated Hepadnavirus mutant with a single mutation affecting the normal function of the DNA polymerase resulting in decreased sensitivity to a nucleoside analogue compared to a wild-type Hepadnavirus, wherein said mutation consists of an amino acid addition, substitution or deletion in the B domain corresponding to amino acid residues 505–529 of a wild-type HBV polymerase.*

*36. An isolated mutant according to claim 33, wherein the nucleoside analogue is selected from the groups consisting of famciclovir, penciclovir and lamivudine.*

*37. An isolated mutant according to claim 33 or 38, wherein the Hepadhavirus is woodchuck hepatitis virus.*

*38. An isolated mutant according to claim 33 or 38, wherein the Hepadnavirus is duck hepatitis virus.*

*39. A method for determining the potential for an HBV to exhibit, relative to an isolated wild-type HBV, reduced sensitivity to an anti-viral agent, said method comprising isolating DNA or corresponding mRNA from said HBV and screening for a mutation in a nucleotide sequence encoding the B domain of HBV polymerase corresponding to amino acid residues 495–535 of a wild-type HBV polymerase, with said mutation resulting in at least one amino acid substitution, deletion and/or addition in said B domain,*

*wherein the presence of such a mutation is an indication of the potential of reduced sensitivity of said HBV to an anti-viral agent.*

*40. An isolated HBV mutant with a single mutation affecting the normal function of the DNA polymerase resulting in decreased sensitivity to a nucleoside analogue selected from the group consisting of famciclovir, penciclovir and lamivudine, compared to a wild-type HBV and affecting the interactivity of an antibody to a wild-type HBV surface antigen, wherein said HBV mutant comprises at least one of*

*(i) a nucleotide sequence of its genome as set forth in SEQ ID NO:17 or a sequence having at least 60% similarity thereto;*

*(ii) a nucleotide sequence capable of hybridising to SEQ ID NO:17 under low stringency conditions at 42° C.;*

*(iii) a mutation in an overlapping portion of open reading frames for DNA polymerase and HBV surface antigen; and*

*(iv) a mutation in a region corresponding to amino acids 118 to 169 and/or 169 to 207 of HBV surface antigen,*

*wherein said mutant contains a Trp/Arg499Glu amino acid substitution in the DNA polymerase and an Asp144Glu and Gly145Arg amino acid substitution in the surface antigen.*

*41. An isolated HBV mutant with a single mutation affecting the normal function of the DNA polymerase resulting in decreased sensitivity to a nucleoside analogue compared to a wild-type HBV and affecting the interactivity of an antibody to a wild-type HBV surface antigen, wherein said HBV mutant comprises at least one of*

*(i) a nucleotide sequence of its genome as set forth in SEQ ID NO:17 or a sequence having at least 60% similarity thereto;*

*(ii) a nucleotide sequence capable of hybridising to SEQ ID NO:17 under low stringency conditions at 42° C.;*

*(iii) a mutation selected from the group consisting of Phe512Leu, Val519Leu, Pro523Leu, Leu526Met, Thr530Ser, and Ile533Leu; and*

*(iv) a mutation in a region corresponding to amino acids 118 to 169 and/or 169 to 207 of HBV surface antigen,*

*wherein said mutant contains a Trp/Arg499Glu amino acid substitution in the DNA polymerase and an Asp144Glu and Gly145Arg amino acid substitution in the surface antigen.*

* * * * *